(12) United States Patent
Aneja

(10) Patent No.: US 7,825,270 B2
(45) Date of Patent: Nov. 2, 2010

(54) INOSITOLPHOSPHOLIPIDS AND ANALOGUES: PHOSPHATIDYLINOSITOL PRODUCTS AND PROCESSES

(75) Inventor: Raijindra Aneja, Ithaca, NY (US)

(73) Assignee: Nutrimed Biotech, Ithaca, NY (US)

( * ) Notice: Subject to any disclaimer, the term of this patent is extended or adjusted under 35 U.S.C. 154(b) by 919 days.

(21) Appl. No.: 11/613,679

(22) Filed: Dec. 20, 2006

(65) Prior Publication Data

US 2007/0142653 A1 Jun. 21, 2007

Related U.S. Application Data

(60) Provisional application No. 60/752,542, filed on Dec. 21, 2005.

(51) Int. Cl.
C07F 9/02 (2006.01)
(52) U.S. Cl. ....................................... 554/78
(58) Field of Classification Search ............ 554/78
See application file for complete search history.

(56) References Cited

U.S. PATENT DOCUMENTS

| | | |
|---|---|---|
| 3,704,254 A | 11/1972 | Aneja |
| RE28,903 E | 7/1976 | Aneja et al. |
| 4,515,722 A | 5/1985 | Yang et al. |
| 4,977,091 A | 12/1990 | Gilmanov |
| 4,997,761 A | 3/1991 | Jett-Tilton |
| 5,100,787 A | 3/1992 | Shimizu et al. |
| 5,214,171 A | 5/1993 | Dijkstra et al. |
| 5,214,180 A | 5/1993 | Ferrari |
| 5,227,508 A | 7/1993 | Kozikowski |
| 5,833,858 A | 11/1998 | Umeda et al. |
| 6,737,536 B1 | 5/2004 | Aneja |
| 6,828,306 B2 | 12/2004 | Sparks |
| 2004/0191304 A1 | 9/2004 | Sprott et al. |
| 2004/0214783 A1 | 10/2004 | Terman |

OTHER PUBLICATIONS

Chen et al., "Asymmertic Total Synthesis of Phosphatidylinositol 3-Phosphate and 4-Phosphate Derivatives", J. Org. Chem. vol. 63, pp. 6511-6522, 1998.*

Aneja R., Chadha J.S., and Yoell R.W. 1971, Fette Seifen Anstrichmittel, 73: 643-651.

Aneja R. and Aneja S.G. 1999 in Advances in Phosphoinositides. Ed. K. S. Bruzik, ACS Symposium Series 718 Washington D.C. 222-231.

(Continued)

*Primary Examiner*—Deborah D Carr
(74) *Attorney, Agent, or Firm*—William Greener; Frederick J. M. Price; Bond, Schoeneck & King, PLLC

(57) ABSTRACT

Embodiments of the invention relate to natural and synthetic inositolphospholipid (IPL) materials, their preparation and applications. They provide compositions of the parent IPL comprising phosphatidylinositol (PI), PI-phosphates (phosphoinositides) and derivatives and analogues, and a process for their production starting from natural IPL. The embodiments further provide functional derivatives of PI for biomedical applications including a platform for drug design and delivery to therapeutic targets in the phosphoinositide mediated cellular signaling and allied cascades. The embodiments pertain to IPL having absolute stereo-structure. The embodiments further pertain to unique IPL and PI product compositions for defined applications, particularly pharmaceutical compositions for prophylaxis and treatment of diseases related to aberrant cellular and nuclear signaling mediated by PI and PI derived phosphates, and associated phosphoinositide specific enzymes including PI-PLC and PI 3-kinase.

21 Claims, 7 Drawing Sheets

Representative structures of the cellular series parent IPL.

OTHER PUBLICATIONS

Aneja R. and Aneja S. G. 2000, Tetrahedron Lett. 41: 847-850.
Aneja R., Cheng J-S, Stoelting D.T. and Zhu W. 2002, ACS National Meeting, Boston, Aug. 18-22, 2002, Abstract No. 395.
Burgess J.W., Neville T. A-M., Rouillard P., Harder Z., Beanlands D.S., and Sparks D.L. 2005, J. Lipid Res., 46: 350-355.
Carter, H.E., Brooks, S., Gigg, R.H., Strobach, D.R. and Suam, T. 1964, J. Biological Chemistry, 239: 743-746.
Carter H.E. and Kisic A. 1969, J. Lipid Res., 10: 356-362.
Carter H.E., Strobach R. and Hawthorne J.N. 1969, Biochemistry, 8: 383-388.
Colacicco G. and Rapport M.M. 1967, J. Lipid Res., 8: 513-515.
Noda N. and Keenan R.W. 1990, Chem. Phys. Lipids, 53: 53-63.

* cited by examiner

Representative structures of the cellular series parent IPL.

Fig. 2

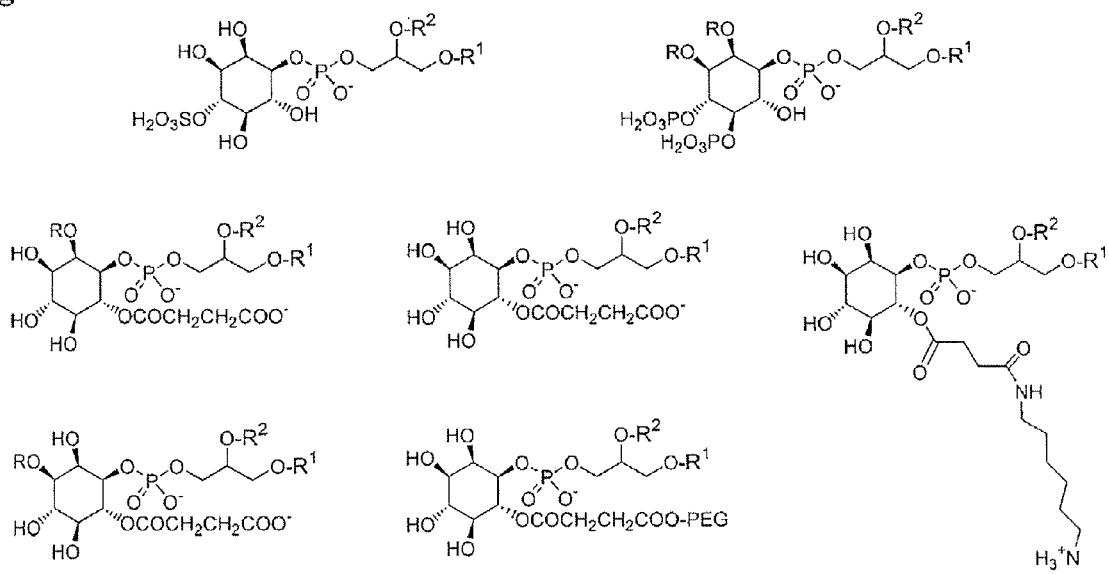

[[R]] RO = Selected from but not limited to Alkyl, [[Alkoxy]] Acyloxy, F, Cl, CN, CH$_2$CH$_2$OH, NHOCR;
[[R$^1$, R$^2$]] R$^1$, R$^2$ = Selected from but not limited to Alkco, Alk, CH$_3$O(CH$_2$)$_n$ Representative structures of PI derivatives carrying additional functional groups;
In analogous structures, C-phosphonate and thiophosphonate groups, replace the
Phosphate in the phosphatidyl residue.

R = H, Protecting group, Linker-Extension, Drug, or Linker-Extension-Drug.
Selected Inositol OH may carry PEG or related O-substituent.

PI-based Vehicles and Drugs for Specific Delivery to Therapeutic Targets in the Phosphoinositide and Allied Metabolic and Signalling Cascades.

Reagents. a: Cyclohexanone dimethylketal, $p$TSA. b: MOMCl, Diisopropylamine. c: MeOH, $p$TSA. d: (iPrN)$_2$P(OFm)$_2$, 1-$H$-tetrazole. e: Bu$_4$NMnO$_4$. f: Et$_3$N. g: HCl. h: EtSH.

Conversion of Soy PI into PI-4,5-bisphosphate.

Reagents. a: Cyclohexanone dimethylketal, $p$TSA.  b: MeOH, $p$TSA

Purification of Soy PI via Protection to Di-O-Cyclohexylidene-PI isomers, and Deprotection to PI.

Fig. 6

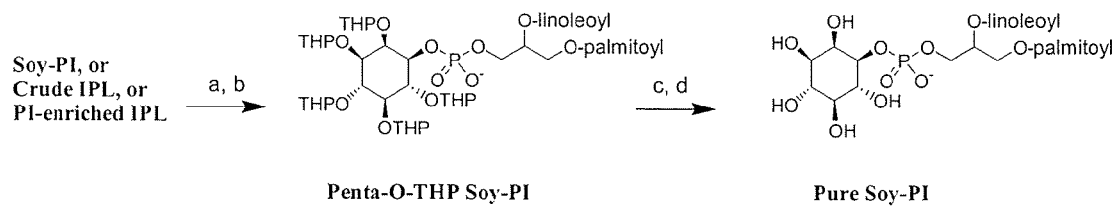

Penta-O-THP Soy-PI           Pure Soy-PI

Reagents. a: 3,4-Dihydro-2H-pyran, pTSA. b: Purification. c: MeOH, pTSA. d: Purification.

Reaction Conditions. Very large excess of 3,4-Dihydro-2H-pyran to preclude successive phosphatidyl migrations from myo-inositol C-1 to C-2, C-3 positions.

Other Protecting Groups. Acid-sensitive base-stable temporary O-protecting group.

Purification via Protection to Penta-O-protected PI and Deprotection to PI.

Acid catalyzed phosphatidyl migration and isomerization.

INOSITOLPHOSPHOLIPIDS AND ANALOGUES: PHOSPHATIDYLINOSITOL PRODUCTS AND PROCESSES

CROSS-REFERENCE TO RELATED APPLICATIONS

The present application claims priority from U.S. provisional application Ser. No. 60/752,542, entitled "Inositolphospholipids And Analogues: Phosphatidylinositol Products And Processes," filed Dec. 21, 2005.

STATEMENT REGARDING FEDERALLY SPONSORED RESEARCH

The present invention was partially made with funds provided by the Department of Health and Human Services under NIH Grant No. GM59550. Accordingly, the United States Government owns certain rights in this invention.

FIELD OF THE INVENTION

Embodiments of the invention pertain to natural and synthetic inositolphospholipids (IPL) materials, their preparation and applications. It particularly pertains to the parent IPL comprising phosphatidylinositol (PI), PI-phosphates (phosphoinositides) and derivatives and analogues, and a process for their production. It further pertains to the molecular design of functional derivatives of PI for biomedical applications including a platform for drug design and delivery to therapeutic targets in the phosphoinositide mediated cellular signaling and allied cascades. The embodiments of the invention further pertain to IPL product compositions for defined applications, particularly pharmaceutical compositions for prophylaxis and treatment of diseases related to aberrant signal via the IPL, particularly the phosphoinositides (phosphatidylinositols and derived phosphates) mediated cellular and nuclear signaling. In all embodiments, it pertains to natural and synthetic IPL comprising PI and its derivatives and analogues having absolute stereo-structure.

BACKGROUND OF THE INVENTION

The IPL are conjugates of an inositol moiety that is regio- and stereo-specifically linked by a phosphodiester bridge to a lipid moiety. Natural IPL generally have structures based on 1D-1-myo-inositol; however, structures based on uncommon inositol isomers, for example scyllo-inositol, are known. Two structural parents in the myo-inositol series are the glycerolipid-based PI wherein the lipid residue is a 1,2-diacylglyceryl-moiety, and, the sphingolipid-based ceramide-phosphoinositols (Cer-PI) wherein the lipid residue is an N-fattyacyl-sphingosine moiety. Cellular PI belong to the 1D-1-myo-inositol series and have the 1D-1-(1-fattyacyl$^1$-2-fattyacyl$^2$-sn-glycero-3-phospho)-myo-inositol absolute stereochemical structure shown. The cellular Cer-PI commonly have the 1D-1-myo-inositol stereochemical structure conjugated to ceramide moiety with a D-erythro-sphingosine stereostructure. Representative absolute structural parent IPL are shown in FIG. 1. These absolute stereo-structures are susceptible to change during physico-chemical processing.

PI, their radyl analogues with alkylether in place of fattyacyl, Cer-PI, and, their derivatives carrying fattyacyl, glycosyl, and phosphate groups covalently linked to the inositol residue, occur as minor components of biological cells. As the name signifies, synthetic IPL, their structural and stereochemical analogues, and their respective derivatives and congeners, are prepared by synthesis.

The IPL are biological and biocompatible amphiphilic materials with diverse roles and uses. The cellular IPL have critical physicochemical, biochemical and physiological functional roles; in particular, PI and derived mono-, di-, and tris-phosphates, the so-called phosphoinositides, are transducers in vital intracellular and nuclear signaling and related processes. The natural, as well as the synthetic products are useful, broadly, as biochemical reagents in studies on the structure and function of cell membranes and mechanisms of intracellular signaling, as reference compounds for analysis of cellular IPL, as substrates in assays and diagnostics kits for enzymes involved in signaling via the IPL, as lead compounds for the design and development of novel drugs for the treatment of disorders caused by aberrant signaling including diabetes and some cancers, as nutraceuticals and drugs for central nervous system disorders and cardiac arterial diseases, for bio-delivery of specific pharmacodynamic fattyacyls covalently incorporated in the phosphoinositide structure, as the lipid component in liposomal delivery vehicles for cytotoxic drugs, bioactive peptides, proteins and polynucleotides, and in cosmetics formulations.

The embodiments of the present invention particularly provide novel IPL materials and compositions, more particularly, PI and structural and stereochemical analogues, and their respective derivatives including but not limited to phosphate derivatives. The invention embodiments additionally provide methods for isolation and purification of IPL, particularly PI, from natural lipid sources, and, further provide a novel process approach for low cost preparation and large-scale production comprising synthesis using natural IPL as starting materials. The present methods of isolation, purification and synthesis uniquely are designed and validated to ensure that the IPL products of the invention retain the core structure and absolute stereochemistry of the natural IPL, in both the myo-inositol and the lipid residues; for PI, this is the 1D-1-(1-fattyacyl$^1$-2-fattyacyl$^2$-sn-glycero-3-phospho)-myo-inositol absolute stereochemical structure.

DESCRIPTION OF RELATED ART

The Inositolphospholipids: Structures, Biological Roles, and Utility

IPL constitute an important group of biological small molecules, which includes the structural parents PI and Cer-PI (Carter et al, 1965). Cellular PI belong to the 1D-1-myo-inositol series and have the 1D-1-(1-fattyacyl$^1$-2-fattyacyl$^2$-sn-glycero-3-phospho)-myo-inositol absolute stereochemical structure. In the radyl analogues (Radyl-PI), the 1-fattyacyl residue is replaced by O-alkyl, and in Cer-PI (and phytoceramide-PI), the 1,2-diacylglycero residue is replaced by a ceramide moiety. The corresponding lyso-series of IPL, Lyso-PI, lack the 2-fattyacyl and thus have a free hydroxyl group at the glycero-2 position. The sphingosyl-phosphoinositols (Sph-PI) lack the amide fattyacyl and have a free 2-amino group in the long chain lipid base, and the fattyacyl may be derivatized further with OH and C=C functional groups. Representative structures of the cellular series are shown in FIG. 1.

As noted above, in cellular PI the inositol moiety is in the 1D-1-myo-inositol and the glycerol moiety is in the sn-glycero-3-phospho configuration. The glycerol residue is esterified with mixtures of saturated long carbon chain fattyacyls, and unsaturated and polyunsaturated fattyacyls collectively referred to as (poly)unsaturated fattyacyls. Thus, PI in natural phospholipids are complex mixtures of molecular species differing in their fattyacyl composition and distribution between glycero-1 and -2 positions. In the naturally occurring Cer-PI (and phytoceramide-PI) series, the sphingosine/ceramide residue has the D-erythro stereochemical configuration. Cer-PI show variable chain length and degree of unsaturation in the two alkyl groups of the ceramide residue, and may carry additional OH, C=C and/or related functional groups. Synthetic PI analogues are based on the sn-glycero-3-phospho as well as the sn-glycero-1-phospho configurations, and the synthetic analogues of Cer-PI are based on the D-erythro, L-erythro, D-threo, or L-threo stereochemical configurations in the sphingosine/ceramide residues. Diastereomers are formed by all combinations of the 1D-1- and 1L-1-myo-inositols with the aforementioned glycerol or sphingosine/ceramide configurations. This invention pertains to all such stereochemical combinations.

In eukaryotic cells, PI are quantitatively minor but vital components of membrane lipids with critical structural and metabolic roles. In the structural role, PI function akin to the more abundant phosphatidylcholines and phosphatidylethanolamines in membranes (Small, 1986) but this has not been studied in detail. In its metabolic roles, PI is the parent participant in the vital PI cycle, which is responsive directly to various extra cellular stimuli acting on the cell (Hokin, 1985). Agonist stimulated metabolism is mediated by combinations of many regulatory protein and enzyme families including the PI transfer protein, PI synthase, and phospholipases, kinases and phosphate-phosphatases specific for the PI group implicated in intracellular signaling. Mono-, bis-, and tris-phosphates of PI are formed and their cellular concentrations are regulated by the actions of kinase and phosphate-phosphatase groups of enzyme families, which are specific for the 3-, 4-, or 5-positions. The action of PI specific phospholipase C (Rhee et al, 1989) on PI-4,5-bisphosphate generates the intracellular second messengers inositol-1,4,5-trisphosphate and diacylglycerol which respectively mediate release of intracellular Ca ions (Berridge, 1984, 1987, 1993) and activation of protein kinase C (Nishizuka, 1986) respectively. The 3-phosphate series (Whitman et al, 1988) act as messengers in mitogenic and related signals more directly (Toker et al, 1994; Duckworth and Cantley, 1996). Action of cytosolic phospholipase $A_2$ liberates arachidonic acid from the sn-glycero-2-O-acyl moiety (Lapetina et al, 1981) which is utilized in the arachidonic acid-eicosanoid messenger cascades. Thus, PI is a direct and indirect reservoir of additional signaling molecules, which mediate and control vital cellular functions (Bell et al, 1996). PI moiety is the lipid component in glycosyl-PIs which function as membrane anchors of important cellular proteins (Englund, 1993), and as transducers in the insulin messenger cascade (Saltiel et al, 1986). The radyl and sphingo analogues of PI and glycosyl-PIs have similar and additional roles (Ferguson and Williams, 1988). Synthetic IPL and analogues are used as research reagents in multifarious signaling and related biomedical fields. PI as the amphiphiles in liposomal drug delivery vehicles prevents recognition of vesicle surface by the phagocytic cells of the reticuloendothelial system, the circulating mononuclear phagocytic cells and located in liver and spleen, and enhances blood circulation time of the drug formulation (Lee et al, 1992).

Plant PI has a dramatic toxic effect on numerous tumor cells lines but not on normal cells (Jett et al, 1985). Difference between PI types have been attributed to the fattyacyl composition, particularly at the sn-glycero-2-O position (Jett et al, 1985). Plant PI, specifically Soy PI, also was reported to have antiviral activity and recommended as a prophylactic for HIV; the identity of the fattyacyl in the sn-glycero-2-O-position appears critical for activity (Jett-Tilton, 1991). Plant PI has beneficial therapeutic effects for central nervous system disorders including depressions and pharmacologically induced memory alterations (Ferrari, 1993, U.S. Pat. No. 5,214,180).

More recently, attention has been on developments based on inhibitors and modulators of the phospholipases, kinases, and phosphate phosphatases involved in signal transduction. PI analogues modified in the inositol-2-position, for instance the 2-fluorodeoxy-scyllo-inositol types, were found to be effective inhibitors of phospholipase C and potent anti-inflammatory and analgesic agents (Yang et al, 1985). 2-Modified phosphoinositides in general have analogous potential as lead compounds for the development of therapeutics relying on the inhibition of PI-specific phospholipase C (PI-PLC) (Aneja and Aneja, 1999). Other inhibitors of PI-PLC are based on the thiophosphate and phosphonate analogues. The water soluble D-myo-inositol 4-(hexadecyloxy)-3(S)methoxy-butane-phosphonate, a phosphonate analogue of PI, is reported to inhibit epithelial cell proliferation (Leung et al, 1998a). PI analogues modified at the inositol-3-position inhibit the growth of mammalian cells, and have potential for treating neoplastic conditions and other proliferative disorders (Kozikowski et al, 1993, U.S. Pat. No. 5,227,508). Inhibitors of ceramide-phospho-inositol synthase are potent antifungal agents (Mandala et al, 1998).

Early studies on the effects of PI on serum lipids and lipoproteins in relation to cardiac arterial disease (CAD), especially mobilization of cholesterol to the blood stream and development and resorption of atherosclerosis, gave conflicting results (Sachs et al, 1960, and references therein). Very recently, it was reported that administration of PI stimulates reverse cholesterol transport by increasing the flux of cholesterol into high density lipoprotein-cholesterol (HDL-C), raises HDL-C levels in humans, and suggesting that PI administration has a therapeutic benefit in CAD (Sparks, 2004, U.S. Pat. No. 6,828,306; Burgess et al, 2005).

Significant quantities of IPL, particularly PI, derivatives and analogues are required for aforementioned application areas, including but not limited to use as drug delivery vehicles, nutraceuticals, therapeutics, and in the drug cum drug delivery vehicles based on PI that are an integral part of the present invention. All known and upcoming future applications mandate that the IPL and PI products have unequivocally established stereo-structures. In addition, large-scale applications including drug delivery vehicles, nutraceuticals and therapeutics mandate a low production cost. The prior art has not provided natural source PI, particularly plant source PI with unequivocally validated absolute stereo-structure, and at low cost production.

The Preparation of Natural and Synthetic Phosphatidylinositols—Prior Art Relevant to Soy PI Prior art methods for preparing Natural PI from plant sources are outlined below. Recent and prior art on synthesis has been reviewed extensively by the Inventor (Aneja, 2004, U.S. Pat. No. 6,737,536), and is incorporated herein by reference.

Natural PI-enriched fractions have been isolated from soy lecithins by solvent extraction and liquid-liquid partition but the products invariably contain phosphatidylethanolamines (PE) and phosphatidic acid (PA) (Shimizu et al, 1992, U.S. Pat. No. 5,100,787).

A PI-enriched fraction, named lipositol, prepared by multiple precipitations using cold $CHCl_3$ and $CH_3OH$ (MeOH), had a significant Nitrogen content, ascribable to PE (Woolley, 1943); it was confirmed later that the major contaminant in such preparations is PE (Colacicco and Rapport, 1967).

PI-enriched lecithin fractions were prepared by countercurrent distribution but had significant PE, phosphatidylcholine (PC), and allied impurities (Carter and Kisic, 1969).

Relatively pure soy PI was obtained by a composite process comprising solvent extraction, ion exchange on a Chelex 100 resin, column chromatography on silica, and "crystallization" (Colacicco and Rapport, 1967). These, and allied methods using chromatography on dialkylaminoalkyl-ion exchange media diethylaminoethyl cellulose and related matrices, are tedious, costly and not suitable for large-scale production.

A process for recovering PI from grain powders initially produces a PI-protein complex, from which PI is isolated by extraction; it is surprising that the extracting solvent is said to be methanol (Gilmanov et al, 1990, U.S. Pat. No. 4,977,091).

Another process for the preparation of highly pure PI (Ferrari et al, 1993, U.S. Pat. No. 5,214,180), initially converts the PE in lecithin to PC by treatment with base and $CH_3I$, and removes PC by solvent extraction. The residue is treated with reagents selected from the group consisting of dimethyltertbutylsilylchloride, thexyldimethylsilylchloride, trimethylsilylchloride and allyl bromide, to convert PI into alkylsilyl or allyl derivatives. Finally, the alkylsilyl or allyl groups are removed under conditions such as not to modify the phosphatidyl group, but proof about changes, if any, to the absolute stereo-structure of the recovered PI was not provided.

In another process, the starting material is a lecithin, which contains PI as the only IPL material. A PC-free lecithin fraction is first obtained from the starting material by multiple precipitations using $CHCl_3$ and MeOH. This fraction is lipolysed with phospholipase D (PLD) to convert the residual PE into PA, followed by reaction with a phosphatase to convert the PA into diacylglycerol; the resulting mixture of PI and diacylglycerol is separated by solvent extraction and precipitation (Shimizu et al, 1992, U.S. Pat. No. 5,100,787). The diastereomeric purity of the PI product is uncertain because of other reports showing that PI is readily attacked by PLD causing hydrolysis and transphosphatidylation; the transphosphatidylation reaction occurs with PI (as an alcohol) and added alcohols. For instance, it has been reported that reaction between PI and PLD, produces some PA by hydrolysis, but the main products are bis(phosphatidyl)inositols, formed by inter-molecular transphosphatidylation between two PI substrate molecules (Clarke et al, 1981). Accordingly, concomitant intra-molecular transphosphatidylation of PI is expected leading to products containing unchanged PI and PI-isomers and diastereomers.

Overall, prior art processes do not disclose that the product PI retains the absolute stereo-structure of natural PI. To date, none of the prior art methods has been adapted for the production of natural PI.

SUMMARY OF THE INVENTION

The inositolphospholipids (IPL) are conjugates of an inositol moiety, usually a myo-inositol moiety, linked regio- and stereo-specifically by a phosphodiester bridge to a lipid moiety, commonly a 1,2-difattyacyl-glycerol or ceramide. The cellular IPL have critical physicochemical, biochemical and physiological functional roles, for example as transducers in vital intracellular and nuclear signaling. Natural and synthetic IPL have diverse uses in biomedicine, nutrition and food, as reagents for signaling research, enzyme assays, drug discovery, drug delivery, nutraceuticals, and therapeutics.

An embodiment of the invention pertains to natural and synthetic IPL comprising PI and its derivatives and analogues for which unequivocal proof of absolute stereo-structure is provided herein. In one embodiment, this invention relates to natural IPL, their preparation and applications. The invention provides natural IPL materials that are substantially free of non-IPL materials, and have unequivocally established core IPL stereo-structure. The invention particularly provides IPL products that are substantially free of PE and PA. The natural IPL products include compositions enriched in the structural parent PI for which the core absolute stereo-chemical structure is $1_D$-1-(1-fattyacyl$^1$-2-fattyacyl$^2$-sn-glycero-3-phospho)-myo-inositol.

Concomitantly, an embodiment of the invention provides a low cost process for the isolation and purification of the said IPL from natural lipid sources, especially plant seed oil phosphatides and commercial lecithins, and, in a particular aspect, soy lecithins. The process embodies parameters, which demonstrably preserve the core stereo-structure of the natural IPL, including the core absolute stereo-chemical structure $1_D$-1-(1-fattyacyl$^1$-2-fattyacyl$^2$-sn-glycero-3-phospho)-myo-inositol of PI.

Another embodiment further provides unique IPL product compositions for use broadly in biomedical applications; the unique compositions are used as such or as blends with selected materials.

Another embodiment further provides unique IPL product compositions used as starting materials for preparation of natural and synthetic IPLs and rationally designed analogues including PI and derivatives for defined applications.

The embodiments of the invention provide an advantageous low cost process for production of natural IPL, particularly soy PI, comprising isolation from natural lipid sources, and for the conversion of natural IPL into semi-synthetic derivatives and rationally designed novel analogues. It further provides novel natural and synthetic IPL materials and compositions, made directly by the present process, with or without admixing with other lipids and materials.

The embodiments of the invention also provide specific IPL products including soy PI, and its derivatives and analogues carrying additional functional groups or substituents with negative, positive or neutral net charge, including phosphate, thiophosphate, sulphate, carboxylate, ω-aminoalkyl, alkyl, and polyethyleneglycol, and their respective isosteric molecular and functional group analogues, exemplified by but not limited to the structures shown in FIG. 2, and their cell-permeable derivatives and complexes.

The embodiments of the invention further provides novel synthetic PI-based structural classes carrying substituents at the inositol-6-O-position, with or without additional substituent(s) or modification(s) at one or more remaining four inositol hydroxyls (FIG. 2). These PI-based structural classes and libraries are designed as inhibitors of therapeutic targets in the PI and derived PI-phosphate (phosphoinositide) mediated enzyme and effector protein signaling cascades, and as modulators of the biological activity of PI- and phosphoinositide-dependent lipoproteins.

The embodiments of the invention also provide a novel approach integrating drug design and drug delivery, specifically to therapeutic targets in the phosphoinositide and allied metabolic and signaling cascades. This approach is based on a novel molecular design comprising therapeutically active IPL delivery vehicles that are conjugated, via a controlled stability and adjustable chain length linker, to another drug (FIG. 3). The conjugates retain the intrinsic propensity of the IPL for accumulation in vivo in specific lipid-protein complexes and for clustering in special cell membrane domains and thus provide templates for binding specific effector proteins and signaling enzymes. The IPL residue has inherent drug bioactivity towards defined therapeutic targets that include the aforementioned effector proteins and enzymes in the phosphoinositide-dependent metabolic and intracellular signaling pathways. The other drug is bioactive towards therapeutic targets in the phosphoinositides cascade or downstream from the phosphoinositide-dependent metabolic and intracellular signaling pathways; the latter include protein kinases, phosphatases and allied signaling proteins. The physical dimensions, flexibility, and propensity of the linker towards chemical or biochemical rupture ensure that the other drug is either held or released in spatial proximity to the therapeutic targets. This invention specifically provides the said IPL delivery vehicles comprising PI-derivatives conjugated to controlled stability and adjustable chain length linkers, and to second drug.

The embodiments of the invention also provide selectively O-protected PI derivatives that are key precursors and intermediates in synthesis and are utilized herein for the preparation of natural IPL, exemplified by soy PI and Soy PI-4,5-bisphosphate (FIGS. 4, 5 and 6), and the aforementioned rationally designed IPL derivatives and analogues.

Thus, it will be seen that the embodiments of the invention provide the aforementioned novel IPL compositions, particularly PI, derivatives and analogues, O-protected PI derivatives, all with unequivocal stereo-structures.

The embodiments of the invention provide a scalable low cost process approach for the preparation and production of the aforementioned novel IPL, particularly PI, derivatives and analogues, O-protected PI derivatives, all with unequivocally established stereo-structures.

The embodiments of the further pertain to novel unique IPL product compositions for defined applications, particularly pharmaceutical compositions for prophylaxis and treatment of diseases related to aberrant signal via the IPL, particularly the phosphoinositides (phosphatidylinositols and derived phosphates) mediated cellular and nuclear signaling.

BRIEF DESCRIPTION OF THE DRAWINGS

FIG. 2. shows representative structures of PI derivatives carrying additional functional groups;

FIG. 6. shows purification via protection to Penta-O-protected-PI and deprotection to PI.

DETAILED DESCRIPTION OF PREFERRED EMBODIMENTS OF THE INVENTION

Natural Source Lipid Starting Materials

Figure 1:
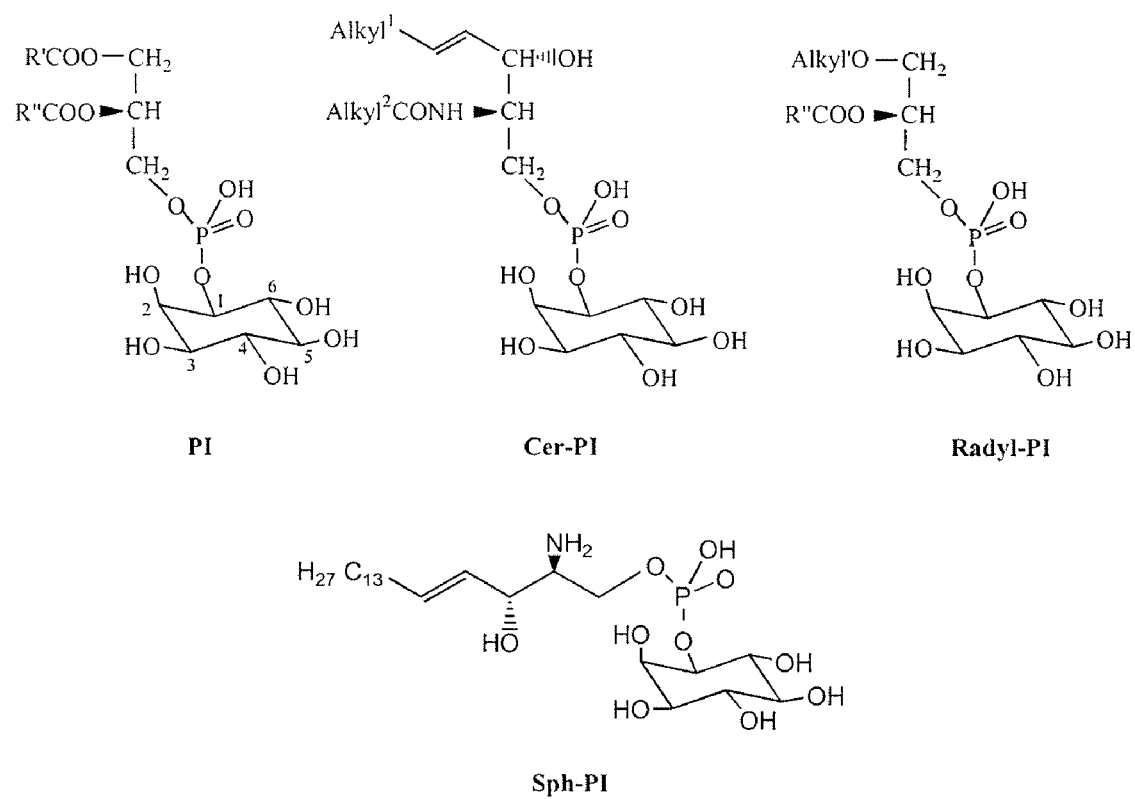
FIG. 1. shows representative structures of the cellular series parent IPL.
Figure 3:
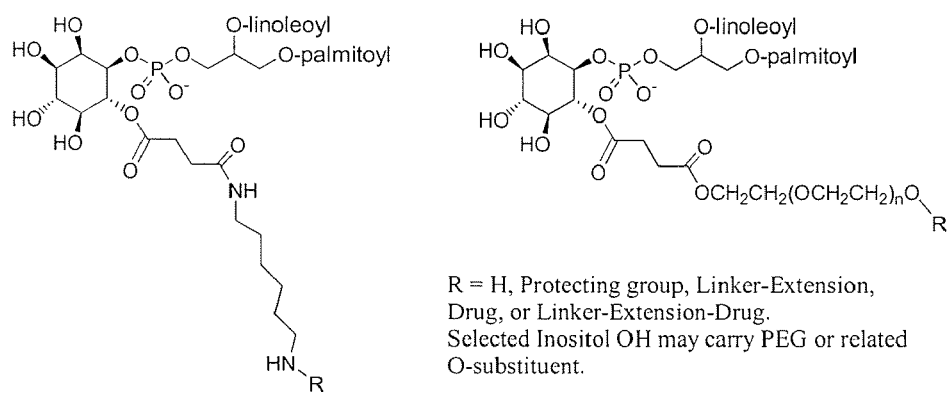
FIG. 3. shows PI-based vehicles and drugs for specific delivery to therapeutic targets in the phosphoinositide and allied metabolic and signaling cascades.
Figure 4:
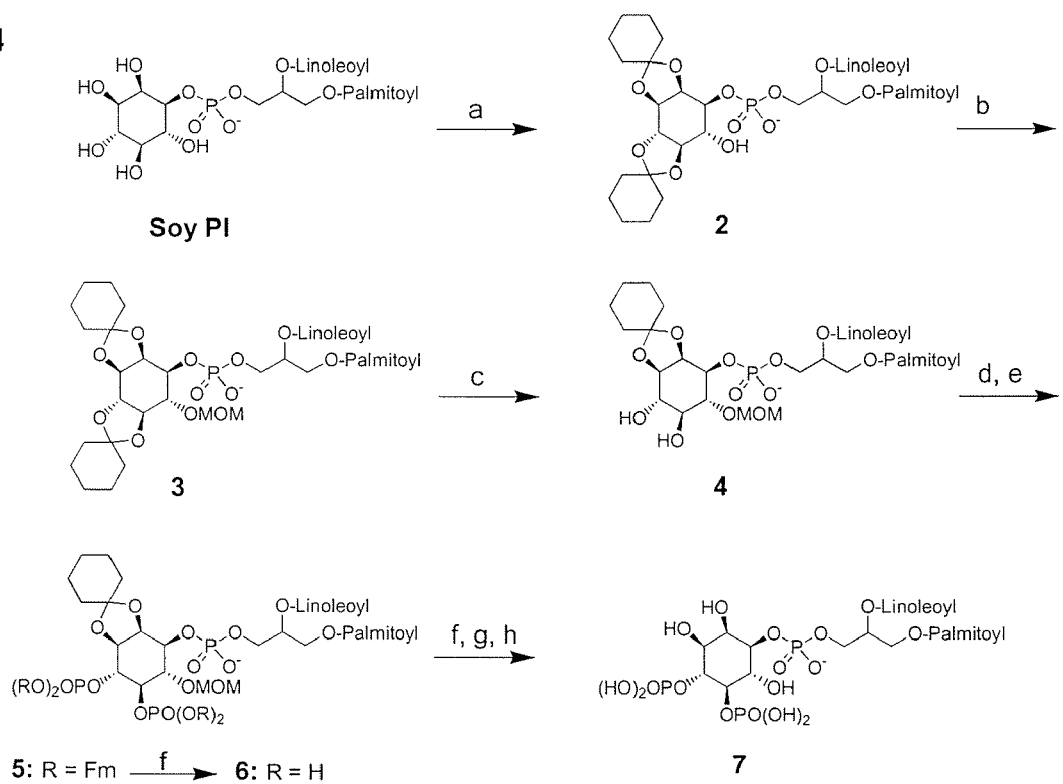
FIG. 4. shows conversion of Soy PI into PI-4,5-bisphosphate.
Figure 5:
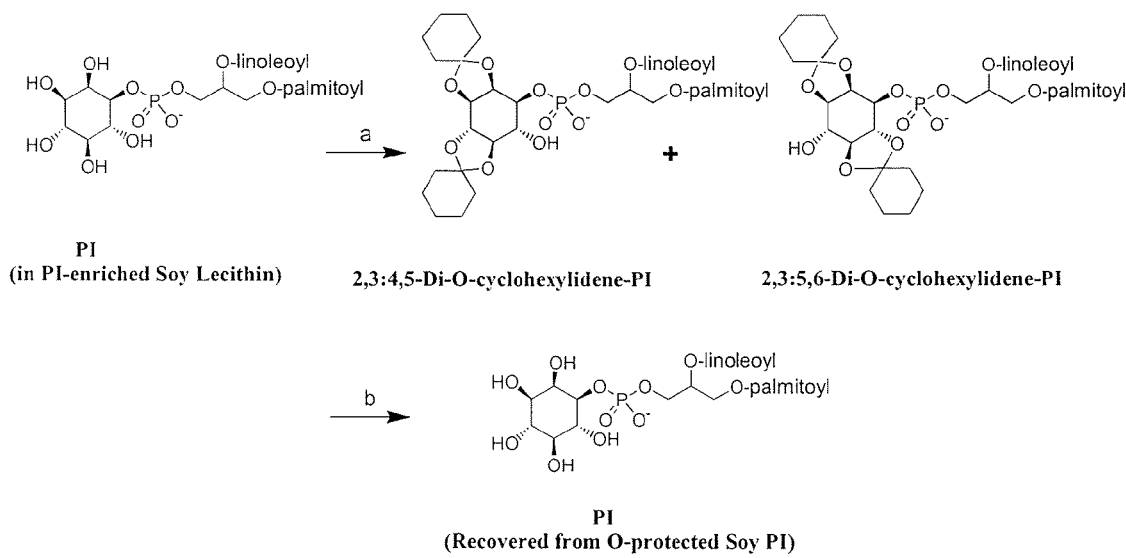
FIG. 5. shows purification of soy PI via protection to Di-O-Cyclohexylidene-PI isomers, and deprotection to PI.

Starting materials for the invention are natural source lipids that contain IPL. These materials are exemplified by phosphatide gums from plant seed oils and the derived commercial lecithins. Plant seed phosphatides are by-products in the production of refined edible oils, and are obtained initially as hydrated gums in the steam-refining step; these are used directly or after dehydration. The dehydrated phosphatide gums are available as commercial plant seed lecithins. Soybean lecithins often are referred to as soy lecithins or simply as lecithins.

Lecithins are available from several commercial sources, and are the preferred starting materials. Commercial lecithins are complex mixtures of natural lipids, and are produced as fluid (liquid), and powder or granulated forms. Fluid lecithins contain triglyceride (TG) as a substantial component, which is removed by selective extraction with acetone or by supercritical fluids to produce de-oiled lecithins. The following composition data for commercial lecithins are typical and are taken from the brochure "Learn about Lecithins" published by American Lecithin Company, Oxford, Conn., U.S.A.

Fluid lecithins: Triglycerides (TG, 37%); Phosphatidylcholines (PC, 16%); Phosphatidylethanolamines (PE, 13%); Phosphatidylinositol (PI, 10%); Phosphatidic Acid (PA, 5%); Minor phospholipids (unidentified, 2%); Glycolipids (11%); Complexed Sugars (5%); Water (1%); Soybean Meal Fines (0.1%).

De-Oiled Lecithins: TG, 3%; PC, 24%; PE, 20%; PI, 14%; PA, 7%; Minor phospholipids (unidentified, 3%); Glycolipids (15%); Complexed Sugars (8%); Water (1%); Soybean Meal Fines (0.2%).

The aforementioned glycolipids and complexed sugars include steryl-glycosides (SG), steryl-glycoside fattyacyl esters (SGE) (Aneja et al, 1974), and, significant amounts of phytoglycolipids (PGL), ceramide-phosphate-polysaccharides (CPPS), and highly polar glycolipids that lack phosphate, and are provisionally identified as glyco-phytosphingolipids (also known as phytocerebrosides) (GSL). PGL are highly glycosylated IPL that have phytosphingosine-based ceramide as the long chain lipid residue (rather than diacylglycerol residue present in PI). The structure of soy PGL presumably is closely related to that proposed for corn PGL wherein the glycosyl residues comprise glucosamine/N-acetylglucosamine, glucronic acid, mannose, and other sugars, and analogues that lack glucosamine/N-acetylglucosamine (Carter et al, 1969). The minor lipids include N-acyl-PE (Aneja et al, 1969), free fatty acids (FFA), and the IPL Lyso-PI.

Other suitable starting materials include lecithin fractions that contain a smaller than typical percentage of PC, PE, PA, and/or PGL and consequently a higher content of PI (Aneja et al, 1971; Aneja, 1972, U.S. Pat. No. 3,704,254; Aneja and Chadha, 1976, U.S. Pat. No. RE 28,903; Ferrari et al, 1993, U.S. Pat. No. 5,214,180). Natural lipids and fractions containing from about 10 to 50% IPL and PI are preferred starting materials.

A natural soy lecithin has been mentioned which apparently contains PI as the only IPL component (Shimizu et al, 1992, U.S. Pat. No. 5,100,787); however, it is a common experience that such compositions are based on inadequate analyses for other IPL which are known components of plant lecithins (Carter et al, 1969). Such lecithin compositions, are desirable starting materials for PI and PI-enriched products.

The Process Approach

The process has a modular design, and comprises selective fractionation of the starting natural lipid mixture by solvent extraction, selective precipitation, and liquid-liquid partition, preferably in conjunction with and aided by solvent modifiers and solute solubility modifiers; optionally, an adsorption step is included. Preferably, the products are isolated in sodium salt form. The process parameters are adjustable to obtain desired product compositions and purity. As an additional option, the PI in the IPL material is converted into a derivative, and the derivative is isolated and purified, and finally reconverted into purified PI product.

Process Design for Lecithins as Starting Materials

This embodiment aspect of the invention is illustrated using soybean phosphatides (commercial lecithin) as the natural lipid source.

It is well known in the art that the PC component in lecithins is soluble in short chain alcohols, particularly ethanol and aqueous ethanol, while PE is sparingly soluble and PI and other IPL are practically insoluble. Thus, extraction of lecithins with alcohol produces alcohol-insoluble lecithin fractions which are richer in PI and IPL content than lecithin, but the prior art products invariably contain significant amounts of PE (Carter and Kisic, 1969, and references therein). We now have discovered that use of certain solubility modifiers can make PE soluble in short chain alcohols without effect on solubility of PI, and that extraction of lecithin using alcohols in conjunction with and aided by solubility modifiers simultaneously dissolve out PE and PC. Additionally, we have discovered that the same solubility modifiers increase the solubility of PA. This discovery has provided a critical basis for the design and development of present process for isolation and purification of IPL and PI from lecithins. Fatty acid anhydrides and equivalent chemical or enzymatic N-acylating reagents are employed as solubility modifiers, with butanoic anhydride and acetic anhydride as the preferred reagents; the latter is the most preferred, inter alia because of low cost, desirable solubility and related physical properties, and the fact that its only by-product is acetic acid.

The process includes three main (Fractionation) and two ancillary (Characterization and Finishing) modules. Further, the process includes an optional module requiring temporary reversible chemical modification of PI in the starting lipid materials.

These modules are identified below and, thereafter, described in detail.

Module 1. Selective Solvent Extraction Aided by Modifiers

Module 2. Selective Solvent Partition

Module 3. Selective Precipitation, Adsorption on Silica, Crystallization

Module 4. Characterization

Module 5. Finishing

Module 6. Purification of IPL via Temporary Reversible Chemical Modification

Module 1. Selective Solvent Extraction Aided by Modifiers

The starting phosphatides or Soy lecithin, or a solution thereof, is treated with acetic anhydride, the reaction mixture is poured slowly into stirred ethanol, and the precipitated alcohol-insoluble material is separated from the alcohol-soluble extract solution. The foregoing extraction and separation sequence is next carried out using the precipitate, or a solution thereof, and is repeated with each successive precipitate, usually from 2-6 times; acetic anhydride is employed in one to three extractions. The process is complete when analysis shows that the precipitate is substantially free of components that are less polar than PI, as judged by thin layer chromatography (TLC) (larger $R_f$ than PI on Silicagel G plates, developed with $CHCl_3$—$CH_3OH$—$NH_4OH$ mixtures, typically 60:40:10, v/v/v). The final precipitate is designated as the 'Total-IPL' product.

The actual yield of Total-IPL ranges from about 50-100% of the theoretical yield calculated for a virtually complete removal of TG, FFA, SG, SGE, PC, and PE, and a partial removal of PA, and some IPL, from the starting soy lecithin composition.

The exact composition of Total-IPL product depends on the composition of the starting material and the conditions for extraction. Typically, Total-IPL contains 20-65% PI, together with PGL, GSL, and minor amounts of PA, and, it is substantially free of TG, FFA, SG, SGE, PC, and PE. This composition specification distinguishes Total-IPL from the alcohol-insoluble fractions of lecithins described in the prior art.

Total-IPL precipitate is processed further in the succeeding modules (Modules 2-5), or utilized in the optional Module 6.

Affect of Acetic Anhydride: Treatment of lecithins with acetic anhydride converts any component structures with free amino functional groups into the corresponding N-acetyl derivatives. Thus, PE is converted into N-acetyl-PE and TLC (Aneja et al, 1971) detects this change easily. Acetic anhydride-treated lecithins, called 'acetylated lecithins', are marketed in the food additives industry and are considered GRAS. Related N-fattyacyl analogues occur, as minor components in plant seed lecithins and the N-acyl-PEs of soy lecithin have been characterized (Aneja et al, 1969).

Under certain conditions in the presence of base or strong acid catalysts, treatment with acetic anhydride also can acetylate free OH and other functional groups. In the present process module, treatment with acetic anhydride is carried out under conditions which exclusively acylate free amino groups and preclude esterification of free alcohol OH groups in PI and other IPL. Reaction is carried out at relatively low temperatures (18-40° C.) for a short time (30-90 min), and monitored by TLC for N-acetyl-PE/PE ratio. These preferred conditions were established in model studies; specifically, it was shown that the PI obtained from acetylated lecithins by chromatography, is identical with natural PI based on rigorous comparison of TLC, MS, NMR and optical rotation data.

In the present process, neat fluid lecithins are treated with acetic anhydride without or with a partial vacuum, to distill out the by-product acetic acid and thereby force the reaction to near complete conversion of PE to N-acetyl-PE. However, complete conversion to N-acetyl-PE is not necessary. Both fluid and de-oiled lecithins are acetylated in solvents, especially hexanes or hexanes mixed with other solvents selected from acetone, ethyl acetate or ethanol. Acetylation in the presence of ethanol reduces any proclivity for acetylation of free hydroxyls of IPL and glycolipids. Under the conditions noted, PE to N-acetyl-PE conversion reaches 90%; no base catalyst is necessary, but the usual inorganic, polymeric or small molecule bases may be employed provided acetylation of OH groups is avoided. It is noted that most small molecule base catalysts exemplified by $NEt_3$ should be excluded because of toxicity concerns.

Acetic anhydride, and other fatty acid anhydrides, surprisingly also facilitate extraction of PA. The mechanism for this facilitation is not understood but is ascribable to the potential in situ formation and high solubility of the acyl-phosphoric mixed anhydride species in certain solvents, notably EtOAc, alone and in mixture with other solvents; it is noted that mechanistically no net chemical transformation of PA is expected and none is overtly observed.

Solvents for Fractionation: Fractionation of lecithins by selective solvent extraction and precipitation was described above using hexanes to dissolve and short chain alcohols, particularly ethanol, to cause selective precipitation. Extraction with supercritical fluids is equivalent. Combinations of pairs of relatively non-polar and polar solvents, are employed also, and include but are not limited to hydrocarbons, halogenated hydrocarbons, and low molecular weight alkylesters, ketones, and alcohols. Improved results are obtained when successive extractions are carried out with different solvent pairs. As an example, extraction and precipitation with the hexanes-ethanol followed by $CHCl_3$—$CH_3OH$, reduces the residual PC, PE, N-Acyl-PE, PA and other minor non-IPL materials in Total-IPL product compared with use of hexane-ethanol alone. As expected from the Distribution Law, a single extraction with a large solvent volume is less efficient than multiple extractions with fractional volumes. The relative volumes of each component of the solvent pair, in proportion to the lecithins, are determined by pilot experiments with a range of volumes of each component, and monitoring the efficiency and selectivity by TLC of the dissolved (supernatant) and precipitated (pellet) fractions. The said relative proportions are also determined by the ability of the pair to form two and multi-component azeotropes, density, initial cost and cost of recovery and reuse. Extraction with EtOAc-EtOH is advantageous and preferred. These advantages are related to differences in solvent strength and relatively solubility parameters. Extractions may be carried out in any suitable equipment, including Soxhlet types.

In place of selective solvent extraction and precipitation, functionally equivalent operations are employed also; each aided by solvent and solubility modifiers. The functionally equivalent operations include but are not limited to liquid-liquid, including supercritical fluid, partition. Preferably, these operations are carried out in conjunction with and aided by solvent and solubility modifiers. Solvent modification is achieved by change of water-content, operational pH and ionic strength, by inclusion of water, salt solution, acids or bases, for example NaCl, acetic acid, phosphoric acid, and $NEt_3$. Use of fatty acid anhydrides, particularly acetic anhydride for solubility modification of PE, is a critical operation as discussed in a previous section (N-Acetylation/Acylation).

Module 2. Selective Solvent Partition

Module 2 starts with Total-IPL from Module 1, and provides an IPL product that is substantially free of the polar glycolipids GSL; overall, the product, GSL-free IPL, is substantially free of GSL as well as of PA, PC, PE, TG, FFA, SG, and SGE removed in Module 1. Module 1 and Module 2 may be integrated to provide the GSL-free product directly. The resulting GSL-free IPL is more highly enriched in PI than Total-IPL; it contains between 50-80% PI, and, may contain only a fraction of the original PGL, PA, and Lyso-PI.

Typically, Total-IPL is dissolved in $CHCl_3$, $CH_3OH$ and water to form two liquid phases. The $CHCl_3$-rich phase is separated, and washed with fresh $CH_3OH$-water phase. GSL partitions selectively into the upper aqueous-methanol layer, the washed $CHCl_3$-rich lower phase is substantially free of GSL, and may be depleted in PGL as well. If insufficient proportions of solvents to solute are employed, GSL and PGL also separate out as a ppt. The layers are separated, the $CHCl_3$-rich lower phase is filtered through Celite, evaporated under reduced pressure to obtain the GSL-free IPL product. The solvent partition comprising aqueous wash as outlined above is effective with a broad range of polar and non-polar solvent pairs, in combination with water or an aqueous salt solution. The solvents are selected from but not limited to hydrocarbon, halogenated hydrocarbon and alkylester, and ketone, short chain alcohol types, and are used in volume proportions that form two liquid phases with added water. Additionally, aqueous solutions of alkali metal salts, including but not limited to sodium salts, preferably NaCl and $Na_4$-EDTA, are used to influence IPL partition and effect concomitant cation-exchange to replace the endogenous $Ca^{++}$ and $Mg^{++}$ counter-ions of IPL with $Na^+$ cations. The cation content in the products, if desired, is determined by Atomic Absorption or equivalent techniques.

Total-IPL solute to the less polar solvent w/v ratio ranges from 1:100 to 1:5, preferably 1:0 to 1:20; as noted above, at low solvent ratios, a GSL/PGL-rich precipitate may form; when Module 1 and Module 2 are integrated, the said w/v ratio up to 1:1000 is employed. Depending on the solvent combinations selected, the GSL component selectively distributes into either the water-rich phase (e.g., chloroform-methanol-water) or the water-poor phase (e.g., hexane-ethanol-water). The GSL-free IPL product is isolated from the appropriate liquid phase, typically by evaporation under reduced pressure, or the product phase is used as such in Module 3.

Module 3. Selective Precipitation, Adsorption on Silica, Crystallization

Module 3 provides IPL products, which are partially or substantially free of PGL in addition to being substantially free of GSL (removed in Module 2) as well as substantially free of PA, PC, PE, TG, FFA, SG, and SGE (removed in Module 1). PGL-free IPL contains 70-95% PI together with, minor amounts of PGL, PA, Lyso-PI and other components. Pure PI from this module is 95-99% pure.

The module comprises selective precipitation for separation of IPL components. Typically, the $CHCl_3$-rich phase from Module 2 containing GSL-free IPL, is cooled, diluted with cold $CH_3OH$ and kept cold (0-5° C.). A precipitate rich in PGL is formed; the supernatant containing the PGL-free IPL is recovered by filtration (filter aid, Celite) or centrifugation. This selective precipitation is repeated, if necessary. The filtrate or supernatant, is evaporated under reduced pressure to obtain the PGL-free IPL, or subjected to selective adsorption on silica.

Further purification to obtain pure PI is carried out by selective adsorption on silica of any remaining PGL and GSL from the PGL-free IPL product. Selective adsorption on silica is employed also to obtain PGL-free IPL product from Total-IPL or GSL-free IPL products. GSL-free IPL in solution, preferably the filtrate or supernatant obtained at the selective precipitation stage, is treated with activated chromatographic grade silica, the solution is filtered through a shallow bed of chromatographic silica, and evaporated to obtain the PGL-free IPL product. Effective solvent mixture compositions are selected by experiment. Mixtures of solvents, selected from those used in Module 2 and exemplified by $CH_3Cl$ and $CH_3OH$, with water or aqueous $NH_4OH$ are effective. The NaCl-washed $CH_3Cl$-rich phase or the supernatant from selective precipitation at the last stage in Module 2 are preferred, and are used directly, or after some adjustment of solvent composition to allow selective adsorption on silica of components with greater polarity than PI.

Adsorption on silica is carried out, and pure PI is obtained, by flash chromatography of Total-IPL or GSL-free IPL, or preferably of PGL-free IPL, using $CH_3Cl$—$CH_3OH$ or hexanes-IPA together with water or aqueous $NH_4OH$ as the elution solvents. Pure PI is eluted, for example with $CHCl_3$—$CH_3OH$—$NH_4OH$ (65:25:3 to 60:40:10, v/v/v).

Module 4. Characterization

The products are characterized by TLC. PI content is measured gravimetrically using PI recovered by column chromatography on silica. The chromatographically isolated PI is characterized by MS, $^1H$ and $^{31}P$ NMR, and, most critically by Optical Rotation (Specific and Molar Rotation) data compared with pure Soy PI isolated from de-oiled soy lecithin by chromatography, as discussed further under Module 6. Fatty acid composition of pure PI is obtained by acid catalyzed methanolysis, and isolation and identification by GC.

Module 5. Finishing

The products of Modules 1-3 preferably are isolated as sodium salts. Optionally, either PGL-free IPL or Pure PI in sodium salt form is subjected to crystallization under conditions that are known in the prior art.

Solvent residues are removed by continuous evacuation under high vacuum. Alternatively, and preferably the products are lyophilized from aqueous dispersions; these lyophilized products disperse easily in water for efficient intestinal absorption.

Module 6: Purification of IPL via Temporary Reversible Chemical Modification

The general process approach purifying IPL from natural lipids is presented herein, and outlined in the Scheme in FIG. 6, with a focus on the preparation of pure PI.

In Module 6, a natural lipid fraction that contains PI and is substantially free of components with polarity lower than PI, is used as the starting material. The starting material is treated (FIG. 6, Step a) with reagents to affect temporary O-substitution of the inositol hydroxyls of PI with base-stable acid-sensitive O-protecting groups. The reaction yields an O-protected PI intermediate, which is O-deprotected to regenerate PI (FIG. 6, Step c). The PI product is characterized to ascertain unequivocally that it has retained the core stereo-structure of natural PI.

According to an aspect, the said PI-enriched natural lipid fraction is from seed phosphatides or commercial lecithins, particularly Soy lecithin. The IPL compositions obtained in Modules 1, 2 or 3 of the present invention, are substantially free of components with polarity lower than PI, and are the most preferred starting materials.

The O-protected PI intermediates are designed to have a polarity lower than PI, and to be easily soluble in solvents that are poor solvents for PI and associated polar IPL components, and do show these properties. The intermediates are separated easily from the reaction mixture by solvent extraction or flash chromatography on silica if components with similar polarity and solubility are not present. Lecithins that are not substantially free of components with polarity lower than PI, are less suitable starting lipid materials than IPL compositions similar to those provided by Modules 1, 2 or 3.

The reagents for introducing the base-stable acid-sensitive O-protecting groups are selected from mono-, di- and tri-functional reagents. These include but are not limited to acetal, ketal, and orthoformate types, exemplified by 3,4-dihydro-2H-pyran (DHP), cyclohexanone-dimethylketal, 1-methoxycyclohexene, and trimethylorthoformate. The O-protecting groups are exemplified by tetrahydropyranyl (THP), tetrahydrofuranyl (THF), 4-methoxy-THP, cyclohexylidene, 2-methoxy-cyclohexyl, acetonide, and methoxylmethyl (MOM). Most of these are introduced at relatively low temperatures in acid catalyzed reactions in anhydrous alcohol-free media. The MOM is introduced using MOMCl in the presence of a hindered tert. amine. DHP, the reagent for introducing THP is available readily, and is inexpensive.

The O-protecting groups are subsequently removed (FIG. 6, Step c) by mild acid catalyzed hydrolysis or alcoholysis of the ketals without damage to long-chain fattyacyl-esters and the overall PI stereostructure. Typically, the O-protected-PI is treated with aqueous alcoholic medium, in a particular aspect in aqueous ethanol or tert-butanol, acidified with p-TSA or equivalent insoluble acid, more particularly Nafion®. The acid catalyst is neutralized, according to an aspect, with aqueous $NaHCO_3$ solution. Undesirable side reactions are minimized by varying the solvent, acid, temp., and time parameters to obtain pure PI directly without need for extensive purification. Alternatively, anhydrous EtSH is used as the solvent and a Lewis acid, such as BF3-ether complex, or a protic acid, e.g. p-TSA, as the acid catalyst at −20° C. to rt.

Very good to excellent yield are obtained in both the O-protection and O-deprotection steps.

Reaction conditions for O-protection and deprotection are employed which demonstrably yield O-protected PI intermediates and final PI products with the natural 1D-1(1,2-diacyl-sn-glycero-3-phospho)-myo-inositol stereo-structure; these reaction conditions are defined and are a particularly distinguishing feature of the present process.

It is noted that isopropylidene derivatives have been prepared from pure PI obtained from Baker's yeast but these derivatives have not been used as intermediates for recovering the intact original natural PI (Noda and Keenan, 1990)

p-TSA catalyzed treatment of pure Soy PI (FIG. 6) with a very large (100 to 200×) molar excess of DHP, used both as solvent and reagent, yielded one major product, identified as penta-O-THP-PI; the same product was obtained in other experiments employing $CH_2Cl_2$ or other inert solvents and a similar large excess of DHP. In contrast, mixtures of partially O-protected O-THP-PI derivatives were formed when only a moderate excess (up to 10 molar) of DHP was employed.

The major product from reaction between pure Soy PI and an enormous excess of DHP, was purified by chromatography on silicagel, using chloroform-methanol-$NH_4OH$ as eluent, and characterized by ES-MS, NMR and optical rotation as the fully O-protected penta-O-THP-PI derivative (FIG. 6). NMR data indicated that the product was a mixture of diastereomers. It is noted that the reaction generates diastereomer mixtures because a new asymmetric center is created with the formation of each of five O-THP links, and furthermore that the existence of the diastereomeric mixture does not affect the stereochemical integrity of the core PI stereo-structure in the product.

In the subsequent O-deprotection reaction step, significantly different results were obtained with the penta-O-THP-PI derivative obtained with a large excess of DHP, contrasted with reaction of the aforementioned mixtures of partially O-protected O-THP-PI derivatives. Complete O-deprotection (FIG. 6, Step c) of pure penta-O-THP-PI gave a product identical with Soy PI. Notably, optical rotation data for the PI product, comprising the observed specific rotation $[\alpha]_D$+6.2 to +6.3 and molar rotation $[\phi]$+52.8 to +53.9 calculated therefrom, were identical with data for a reference Soy PI, and comparable with the literature values $[\alpha]_D$+6.0 to +6.2 and molar rotation $[\phi]$+51 to +52.8 for Soy PI. Optical rotation data have been established as the cardinal stereo-chemically significant parameters for characterizing PI, and $[\alpha]_D$+6.0 and molar rotation $[\phi]$+51 have been established as bench marks for the 1D-1-(1,2-di-O-fattyacyl-sn-glycero-3-phospho)-myo-inositol absolute stereochemical structure (Aneja and Aneja, 2000; Aneja et al, 2002; Aneja, 2004, U.S. Pat. No. 6,737,536).

Complete O-deprotection of the aforementioned mixtures of partially O-protected O-THP-PI derivatives, obtained using only a moderate excess of DHP, gave a products which were similar to Soy PI but showed $[\alpha]_D$ and molar rotation $[\phi]$ significantly higher than normal values for Soy PI. The data indicate that these PI preparations are contaminated with the 1L-1-(1,2-di-O-fattyacyl-sn-glycero-3-phospho)-myo-inositol diastereomer of natural PI for which $[\phi]$+74 has been established as the bench mark value (Aneja and Aneja, 2000; Aneja et al, 2002; Aneja, 2004, U.S. Pat. No. 6,737,536).

Figure 7:
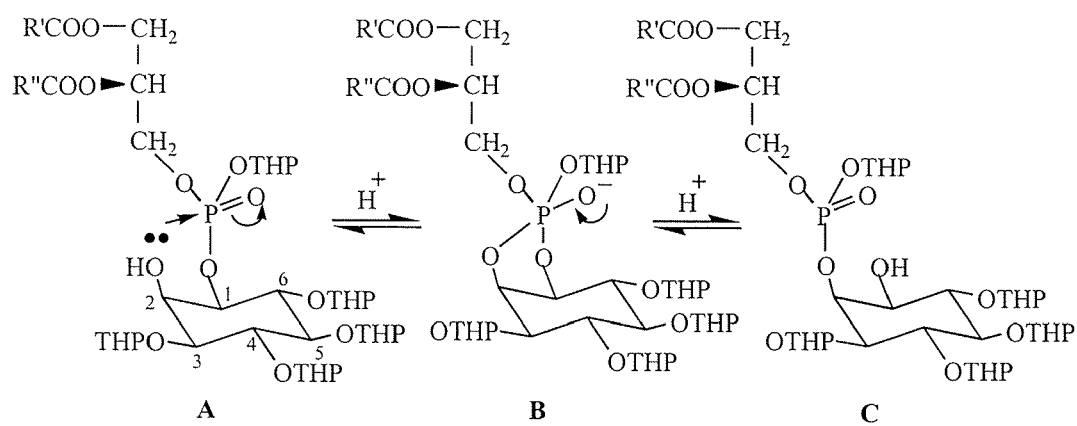
FIG. 7. shows acid catalyzed phosphatidyl migration and isomerization.

The 1L-1-(1,2-di-O-fattyacyl-sn-glycero-3-phospho)-myo-inositol contaminant mentioned above is identical with 1D-3-(1,2-di-O-fattyacyl-sn-glycero-3-phospho)-myo-inositol. Its formation concomitant with the natural 1D-1-(1,2-Di-O-fattyacyl-sn-glycero-3-phospho)-myo-inositol series is rationalized based on the relative reactivity of the various functional groups in PI in reaction with DHP and related reagents (Scheme, FIG. 7). Reactions of the four equatorial hydroxyls at inositol-3,4,5,6-positions, and the phosphoric acid OH, are expected to be faster than axial 2-OH. With low to moderate molar proportions of the O-reactive reagents, partially O-protected intermediates are formed and likely include cis-oriented 2-hydroxy-phosphotriesters carrying a THP esterified to the phosphoric residue; an example is provided in the 3,4,5,6-tetra-O-THP-phosphotriester A shown in FIG. 7. The 1,2-cis-configuration of the free 2-OH adjacent to the phosphotriester at 1-O-position in A facilitates intra-molecular addition-elimination via B or equivalent intermediate structure and leads to isomerization to the 2-phosphatidyl series structure C. The acid catalyzed teterahydropyranylations are reversible and lead to the cis-2,3-configured analogue of B, which in turn is able to equilibrate to the 3-phosphatidyl isomer (structure not shown). Because of the mirror symmetry plane across C-2 and C-5 in myo-inositol derivatives, the 1D-3-phosphatidyl isomer is identical with 1L-1-phosphatidyl diastereomer. Formation and existence of the partially O-protected intermediates with a free 2-OH is obviated when a very large excess of the reagents is employed under conditions which ensure rapid and complete O-protection.

It was mentioned earlier that optical rotation data have been established as the cardinal stereo-chemically significant parameters for characterizing PI. A full discussion of the physicochemical characterization and relationship to the absolute stereochemical structure of PI has been presented and the complete text of the pertinent publications, (Aneja and Aneja, 2000; Aneja et al, 2002; Aneja, 2004, U.S. Pat. No. 6,737,536) is incorporated herein by reference.

Important parameters pertinent to O-protection and O-deprotection include the choice of reagent, reaction medium, catalyst, and conditions for introducing the base-stable acid-sensitive O-protecting groups. In addition, a relatively very large molar excess of the O-protecting reagent over the starting PI is essential for retaining the absolute stereo-structure, and is an integral and distinguishing feature of the present invention. A PI to O-protection reagent molar ratio between 1:100 and 1:200, preferably 1:125 to 1:175 is employed.

In addition to the mono-functional reagent DHP discussed above (FIG. 6), the reaction of PI and the bi-functional reagent cyclohexanone dimethylketal catalyzed by p-TSA was utilized as well. 2,3-Mono-O-cyclohexylidene-PI (not shown) together with 2,3:4,5-di-O-cyclohexylidene-PI and 2,3:5,6-di-O-cyclohexylidene-PI are formed initially followed by the fully O-protected 2,3:4,5-di-O-cyclohexylidene-6-(1-methoxycyclohexyl)-PI (not shown) and 2,3:5,6-di-O-cyclohexylidene-4-(1-methoxycyclohexyl)-PI (not shown). Alternative fully O-protected O-cyclohexylidene-PI derivatives are prepared, for example by reaction of 2,3:4,5-di-O-cyclohexylidene-PI with MOMCl in the presence of diethyl-isopropyl amine. Complete O-deprotection of the various cyclohexylidene-PI derivatives gave PI identical with Soy PI.

Treatment of Pure Soy PI in ether with methanolic tetrabutylammonium hydroxide, gave 1D-1(sn-glycero-3-phospho)-myo-inositol (GPIns), and treatment with phospholipase $A_2$ gave Soy Lyso-PI, useful as biochemical and physiological precursors of PI; these two Soy PI derived products are water soluble and efficiently absorbable in vivo.

Blends

The IPL products optionally are blended with antioxidants, and lipids with synergistic bioactivity, including but not limited to the cardio atheroprotective mono- and diglycerides, ω-3 polyunsaturated and conjugated linolenic acid based lipids of algal and plant origin, phytosterols and derivatives.

Applications

The efficacy of various IPL products and compositions of the present invention is demonstrated by pertinent evaluation protocols described previously, including but not limited to use as drug delivery vehicles (Lee et al, 1992), nutraceuticals and therapeutics for CNS disorders (Ferrari et al, 1993, U.S. Pat. No. 5,214,180) and CAD (Sparks, 2004; Burgess et al, 2005). GPIns and Lyso-PI are water soluble, providing efficient absorption and conversion in the chylomicrons into PI.

Applications of Soy PI in the IPL products and derived O-protected-PIs of this invention as starting materials and intermediates for synthesis of a wide variety of natural and synthetic IPL, and purification of Soy PI, are illustrated in FIGS. 2-6. The rationally designed PI derivatives, carrying functional groups at selected myo-inositol hydroxyl positions, as illustrated by the novel charge neutral, anionic and cationic structures in FIG. 2 are synthesized from 2,3:4,5-di-O-cyclohexylidene-PI as a novel intermediate. The protocols for synthesis are similar to the novel synthesis of Soy PI-4,5-bisphosphate outlined in the scheme in FIG. 4, wherein the fully O-protected 2,3:4,5-di-O-cyclohexylidene-6-O-MOM-PI is critical intermediate. Fully O-protected PI derivatives, exemplified by 2,3:4,5-di-O-cyclohexylidene-6-O-MOM-PI, constitute a novel class designated as "selectively deprotectable O-protected PI derivatives" which were used also for re-tailoring the fattyacyl residues in PI and derivatives by a deacylation cum reacylation cycle. 2,3:4,5-Di-O-cyclohexylidene-PI is also a critical intermediate in the synthesis of novel PI-based vehicles and drug-vehicle conjugates for specific delivery to therapeutic targets in the phosphoinositide-dependent and allied metabolic and signaling cascades, illustrated in FIG. 3; it is also an intermediate for entry into the phosphatidyl-D-chiro-inositol series. Soy derived PI-4,5-bisphosphate is applied, as a reservoir precursor of PI-3,4,5-trisphosphate and related 3-phosphorylated phosphoinositides, in cell and nuclear membrane permeable derivative form, and as novel complexes with functional peptides and proteins forming reconstituted lipoproteins, illustrated by complexes with therapeutic proteins insulin, leptin and apoA.

The following examples are included to demonstrate certain illustrative and preferred embodiments of the invention. It will be appreciated by those of skill in the art that the techniques disclosed in the examples that follow represent techniques discovered by the inventor to function well in the practice of the invention, and can thus be considered to constitute certain of the preferred modes for practicing various aspects of the invention.

EXAMPLES

General Procedures

All operations and reactions were carried out under an inert gas blanket, usually $N_2$ or Argon, and with deoxygenated solvents. Solvents were removed and recovered by rotary evaporation under a vacuum at or below 35° C. bath temperature. Solvent-free materials were obtained by continuous evacuation under a high vacuum. The progress of separations and reactions was monitored by TLC, using Silicagel G on glass or other precoated plates described in the examples. New synthetic compounds were characterized fully using products judged to be >99% pure by TLC. Satisfactory MS (ES, MALDI-TOF) and $^1$H NMR (400 MHz) data conforming to the assigned structure were obtained for all new compounds.

Fluid lecithin refers to commercial fluid soy lecithin (containing ca. 10% PI, 37% TG), typically Alcolec S from American Lecithin Company. Further, de-oiled lecithin refers to commercial lecithin granules or powder (containing ca. 14% PI, 3% TG), from American Lecithin Company, Central Soy, or Degussa.

Reference Soy PI was obtained from the alcohol insoluble fraction of soy lecithin by chromatography on silica eluted with a gradient of $CHCl_3$—$CH_3OH$—$NH_4OH$.

Example 1

This example shows that use of acetic anhydride facilitates extraction of PE and PA from lecithin into solvents that dissolve PC and other components with lower polarity than PI, but do not dissolve IPL.

Comparative Solvent Extraction of Acetylated Lecithins and Lecithins

A mixture of de-oiled lecithin (100 mg) in EtOAc (2.5 ml) and acetic anhydride (10 µl) was held in a 70° C. water bath. After 60 min., EtOH (2.5 ml) was stirred in, and the mixture kept in 70° C. bath for 10 min., removed from the bath, allowed to cool to rt, and centrifuged (5000 RPM, 20 min). A gummy pellet was obtained and was given the same treatment as the starting lecithin, except that 4.5 ml EtOAc was used, and holding time at 70° C. water bath was 10 min. The second pellet (Total-IPL product, dry wt. 27.9 mg) contained, by TLC spot densities, PI (~40%), PGL+GSL (~50%), and small amounts of PA and components less polar than PI estimated at ca. 2% each.

Concurrent control experiments with de-oiled lecithin were conducted as above except that in one experiment acetic anhydride was not used, and in second experiment acetic acid was used in place of the anhydride; the pellets after two precipitations in each (respective dry wts. 37.5, and 37.1 mg) contained PI, PGL+GSL, and significant amounts of PA and PE.

In other experiments, the starting de-oiled lecithin was replaced by acetylated lecithin (180 mg, each) from Example 2; here also, PE and PA were extracted out and Total-IPL product wt. and composition were very similar to those with de-oiled lecithins.

Example 2

This example illustrates the preparation of acetylated soy lecithin from neat (solvent-free) fluid lecithin, and provides evidence that PI in acetylated lecithin remains unacetylated and retains the absolute stereochemical structure 1D-1-(1,2-di-O-fattyacyl-sn-glycero-3-phospho)-myo-inositol of natural PI.

Preparation of Acetylated Lecithin, and Characterization of Pure PI Obtained

Fluid lecithin (100 g), in an evaporation flask (1 L, R.B.) was treated with acetic anhydride (7 ml), and left rotating on a rotary evaporator under a partial vacuum at 35-40° C. bath temp. The by-product acetic acid was distilled out during 2 hr. TLC showed that PE had been replaced almost completely by a new spot with a higher Rf (no purple stain with Ninhydrin spray reagent, blue stain with modified Zinzadze reagent), coinciding with authentic N-acetyl-PE (prepared from pure PE by reaction with acetic anhydride with $NEt_3$ catalyst). Aliquots of this acetylated lecithin were used in several experiments.

An aliquot of acetylated lecithin (ca. 2 g, in hexanes 2 ml) was stirred into EtOH (160 ml) containing EtOAc (40 ml), the mixture left at 0-5° C. overnight. The supernatant was decanted off, the ppt dissolved in hexanes (6 ml), the solution stirred into cold EtOH (200 ml), held at 0-5° C. for 1 hr, centrifuged (500 RPM, 20 min, 0-5° C.), and, the supernatant decanted off. The pellet dissolved in $CHCl_3$-MeOH—$H_2O$ (6 ml: 1 ml: 0.6 ml), was applied to a chromatography column containing silica (50 g) packed in $CHCl_3$-MeOH—$NH_4OH$ (80:20:2, v/v/v), eluted with the same solvent, followed by $CHCl_3$-MeOH—$NH_4OH$ (65:35:3, v/v/v) which eluted out PI. PI-containing fractions were identified by TLC and pooled, evaporated to dryness, and dried overnight under a continuous high vacuum, gave PI as $NH_4$-salt. Yield 232.9 mg. TLC, Silicagel G, $CHCl_3$-MeOH—$NH_4OH$ (60:40:10, v/v/v), Zinzadze spray, and charring, single spot $R_f$ 0.3. $[\alpha]_D$+ 6.3 (c, 1.0, $CHCl_3$-MeOH 4:1); reference soy PI $NH_4$-salt $[\alpha]_D$+6.3 (c, 1.0, $CHCl_3$-MeOH 4:1); literature, soy PI $[\alpha]_D$+ 6.0 (c, 0.83, $CHCl_3$; Colacicco and Rapport, 1967); literature, soy PI $[\alpha]_D$+6.2 (c, 0.51, $CHCl_3$-MeOH 4:1; Aneja and Aneja, 2000).

NMR spectra ($^1$H and $^{31}$P) of pure PI from acetylated lecithin were identical with reference soy PI, and contained no $C\underline{H}_3CO$ resonance peak.

Example 3

This example illustrates the preparation of the various IPL compositions by each of consecutive Modules 1, 2 and 3, and the pertinent process parameters and conditions, starting with a fluid lecithin.

Preparation of IPL Products from Fluid Lecithin

To fluid lecithin (100 g) (commercial fluid soy lecithin containing ca. 10% PI, 37% TG, from American Lecithin Company), diluted with acetone (30 ml), at rt, acetic anhydride (7 ml) was added with stirring. After 75 min, TLC showed that most of the PE had been converted into N-acetyl-PE. The reaction mixture was added slowly into stirred acetone (1 L). The supernatant was decanted off and the gummy ppt was rinsed with acetone (100 ml). The rinsed ppt was dissolved in hexane (100 ml), the cloudy solution added to stirred EtOH (1 L), the supernatant decanted off and the gummy ppt rinsed with EtOH (100 ml); this precipitation operation was repeated three more times using ethanol, and once each with 1:9 acetone-EtOH and 1:1 acetone-EtOH. The ppt changed from gummy to finely powder when acetone was employed; it was filterable but was isolated by centrifugation (5000 RPM, 20 min, 5° C.-15° C.). The final pellet, Total-IPL, (23.7 g) contained, by TLC spot densities PI (40%), PGL+ GSL (52%), PA (3-5%) and small amounts of Lyso-PI, PC, PE, N-acetyl-PE SGE, and related lipids, estimated at <1% each.

The final pellet, Total-IPL, was dissolved in $CHCl_3$ (200 ml), and mixed with MeOH (200 ml) and 5% aqueous NaCl (120 ml). The lower $CHCl_3$ layer was set aside. The upper aqueous-MeOH layer was washed with the lower $CHCl_3$ layer from a solvent blank prepared by adding $CHCl_3$ (200 ml) to MeOH (200 ml) and 5% NaCl (120 ml). The $CHCl_3$ layer from this wash was added to the $CHCl_3$ layer set aside above. TLC of the upper layer (MeOH—NaCl phase) showed that the GSL was present as the predominant component (a spot at the origin showing no blue stain with modified Zinzadze phosphate visualization spray reagent, but charring darkly at 110° C.). The lower layer (CHCl$_3$ phase) contained ca. 15.6 g material, the GSL-free IPL product; it contained PI (60%), PGL (30%), PA (5%) and smaller amounts of Lyso-PI, PC, PE, N-acetyl-PE, SG, SGE and related lipids estimated at <2% each.

The combined CHCl$_3$ layer containing the GSL-free IPL product was mixed with fresh CHCl$_3$ (133 ml), and then MeOH (1100 ml). The resulting ppt was filtered through Celite filter aid. The filtrate was diluted further with CHCl$_3$ (500 ml) and treated with 5% NaCl (660 ml). The lower CHCl$_3$ layer (ca. 1000 ml) was evaporated to obtain the PGL-free IPL product (7.2 g); it contained PI (~95%), and small amounts of PGL, PA, Lyso-PI, PC, PE, N-acetyl-PE, SG, SGE and related lipids estimated at <1% each.

The ppt was recovered by rinsing the spent Celite with warm CHCl$_3$ (100 ml), and evaporation (3.2 g); it contained PGL as the predominant component (75%) with PI (23%) and PA (2%).

In a cognate experiment, Total-IPL product containing PI (38%), PGL+GSL (~60%), and small amounts of PA and PC (<1% each) was partitioned in CHCl$_3$, MeOH, and 4% NaCl. To the lower CHCl$_3$ layer (18 ml) containing 60-65% PI (36 mg) and 35-40% PGL+GSL, was added chromatographic grade silica (2.5 g), in 0.5 g portions. TLC of the solution showed that the PGL+GSL spot density decreased successively with each addition of silica; the final composition of the supernatant was estimated as PI (90-95%) and PA (~3%), with PGL (<1%).

In other related experiments, the CHCl$_3$-MeOH-aqueous phase partition was carried out with Na$_4$ EDTA followed by aqueous NaCl.

Example 4

This example illustrates the preparation of Total-IPL product and the pertinent process parameters and conditions, starting with de-oiled lecithin.

Preparation of Total-IPL Product from De-Oiled Lecithin

De-oiled lecithin (100 g), was stirred into hot EtOAc (2.5 L) held at 60-70° C., acetic anhydride (10 ml) was added with stirring. After 60 min, EtOH (2.5 L) was added, mixed for 15 min, allowed to cool to rt and centrifuged 4000 RPM, 20 min. The supernatant was decanted off, and the pellet suspended in EtOAc (4.5 L), treated with acetic anhydride (10 ml), and after 30 min EtOH (2 L) was added and the mixture stored under nitrogen atmosphere over the weekend. The supernatant was separated by decantation and centrifugation, and the pellet was suspended in EtOH, centrifuged, re-suspended in EtOAc and evaporated to dryness in rotary evaporator under reduced pressure, followed by high vacuum. The product, Total-IPL, 17.5 g, contained, by TLC spot densities PI (~65%), PGL+GSL (~35%), and less than 2% total of other components.

In a cognate experiment, Total-IPL product was obtained containing PI (~38%), PGL+GSL (~60%), PA (~1%), PC (~1%) and minute amounts of other components. Hexanes (2 ml), EtOH (1 ml), and de-ionized water (50 μl) were mixed with the aforementioned Total-PI product (17 mg) containing PI (38%). The resulting two liquid layers were separated. TLC showed that the lower aqueous-EtOH layer contained mainly PI (~80%) with GSL (~7%), PA (~5%), and small amounts of PC (~2%) and SG (~1%). The upper hexane layer contained mainly PGL+GSL (~85%), PI (~10%), with small amounts of PA (~2%) and PC (~1%). About 67% (~4 mg) of total PI was in the aqueous-EtOH layer. Further, in comparative experiments, the quantity of added water was varied, and in others, different volume ratios of hexanes and EtOH were employed.

Example 5

This example illustrates the preparation of Total-IPL composition and the pertinent process parameters and conditions, starting with de-oiled lecithin.

Preparation of Total-IPL Product from De-Oiled Lecithin

A solution of de-oiled lecithin (1 Kg) in hexanes (1 L), was diluted with EtOAc (2 L), the solution slowly added to stirred ethanol (7 L) containing water (350 ml), the mixture was centrifuged (3500 RPM, 20 min, rt) and the pellet recovered. The pellet dissolved in hexanes (1.3 L), and EtOAc (900 ml) was treated with acetic anhydride (40 ml), maintained at 40° C. for min, and the reaction mixture poured slowly into stirred ethanol (7 L). The operation comprising dissolution, and precipitation was repeated three more times using 1.2 L hexanes and 700 ml EtOAc, including twice with inclusion of acetic anhydride (40 ml), and once without it. The resulting pellet was suspended in EtOH (3.6 L), centrifuged, and dried under a vacuum. The final pellet (194.8 g), Total-IPL, contained PI (ca. 60-65%), PGL+GSL (ca. 35-40%), PA and other minor components (<1% each) judged by TLC spot densities.

Flash chromatography of Total-IPL (8 g) on silica eluted with CHCl$_3$-MeOH—NH$_4$OH (65:3:3, v/v/v) gave PI (5.2 g; 98%).

Example 6

Soy PI-2,3,4,5,6-penta-O-tetrahydropyranyl ether
(FIG. 6)

A mixture of pure Soy PI (5.96 g), DHP (100 ml) as reagent and solvent, and Molecular Sieves 4 Å (2.0 g) was cooled to 0-5° C., anhydrous powdered p-TSA (0.2 g) added, the mixture allowed to warm to rt, and held briefly at 40° C.; the progress towards the desired product was monitored by TLC to completion. An excess of NEt$_3$ was added followed by aqueous NaHCO$_3$, and the mixture evaporated under a vacuum to remove the volatile components. The residue was extracted with CHCl$_3$, and the extract purified by chromatography on silicagel eluted with a gradient of CHCl$_3$—CH$_3$OH—NH$_4$OH gave Soy PI-2,3,4,5,6-penta-O-tetrahydropyranyl ether (7.36 g; yield 85%); −m/z 1253.6 (M−H), −m/z 1281.6, etc. (minor molecular species), [α]$_D$−11.49 (c 0.94, CHCl$_3$). A very minor product eluted subsequently, is tentatively considered to be either hexa-O-THP-Lyso-PI or Soy PI-3,4,5,6-tetra-O-tetrahydropyranyl ether.

Soy PI-2,3,4,5,6-penta-O-tetrahydropyranyl ether dissolved easily in alcohol, acetone, ethyl acetate or methanol.

In other experiments, Total-IPL product was used in place of pure PI. Further, O-protection reaction was performed in an anhydrous inert solvent, for example CH$_2$Cl$_2$, CHCl$_3$, hexanes or EtOAc, using a similarly large molar excess of DHP. With a larger proportion of p-TSA, reaction was rapid at 0-5° C. The reaction in neat reagent is highly exothermic with a tendency to produce polymers if overheating occurs.

Example 7

Re-Conversion of Soy PI-2,3,4,5,6-penta-O-tetrahydropyranyl ether into PI (FIG. 6)

The title penta-O-THP-PI was treated with ethanol containing a trace of p-TSA and the reaction monitored by TLC to completion. Purification by chromatography on silica gave a product identical with Soy PI, by ES-MS, NMR and $[\alpha]_D$ as in Example 2.

Characterization

The IPL products were characterized by TLC, MS, $^1$H and $^{31}$P NMR, and optical rotation (specific and molar), as appropriate. Comparative optical rotation data was used as the cardinal parameter for determining absolute stereo-structure and diastereomer composition. Fatty acid composition and distribution was determined by methanolysis, and phospholipase $A_2$ hydrolysis followed by methylation of free fatty acids, and identification and quantitation of fatty acid methyl esters by GC.

Finishing

As noted in the Examples, the products were finished by continuous evacuation under high vacuum. In selected cases, the products were lyophilized, generally as blends with antioxidant. The lyophilized IPL are easily dispersible in water.

Example 8

This example illustrates the preparation, characterization and applications of IPL products comprising phosphatidyl-myo-inositol wherein one or more inositol hydroxyl group is phosphorylated, notably of Soy 1-Phosphatidyl-myo-inositol-4,5-bisphosphate (7) (synthesis Scheme 4) and analogues, as of key O-protected phosphatidyl-myo-inositols as intermediates, and O-substituted phosphatidyl-myo-inositol products.

Soy 1-Phosphatidyl-myo-inositol-4,5-bisphosphate (7)

Soy 1-Phosphatidyl-2,3:4,5-di-O-cyclohexylidene-myo-inositol (2). The total IPL product containing about 65% soy phosphatidyl-myo-inositol (1), prepared as described in Example 4, was heated at ~65° C. with a large excess of cyclohexanone di(ethyl/methyl) ketal and p-toluenesulfonic acid (catalyst) under a slight vacuum. The reaction was monitored by TLC and stopped after 3.6 h of heating by cooling, quenching with triethylamine, and saturated aq NaHCO$_3$ solution, and evaporated at 50° C. under reduced pressure. The residue was purified by chromatography on flash silica gel, eluted with CHCl$_3$/MeOH/NH$_4$OH (v/v/v ratios 95:5: 0.5, solvent 1; 90:10:1, solvent 2; 60:40:10, solvent 3. The material in fractions eluted with solvent 2 contained the two isomeric di-O-cyclohexylidene derivatives (R$_f$ 0.27 and 0.28; TLC, Silica gel G, chloroform/methanol/ammonia 87:11.5: 1.5) was rechromatographed to obtain the pure 1-phosphatidyl-2,3:4,5-di-O-cyclohexylidene-myo-inositol (2); (TLC R$_f$ 0.28); MS (m/z, negative mode) complex set near 993.7 (M−1, acyl groups mainly palmitoyl and linoleoyl), complex set near 1021.7 (M−1, acyl groups mainly stearoyl and linoleoyl). $^1$H NMR (400 MHz, CDCl$_3$) δ 0.88 (m, 6H, CH$_3$), 1.2-1.8 (m, 6H, cyclohexyl and fatty acyl CH$_2$), 1.96-2.1 (m, 4H, allylic CH$_2$), 2.24-2.34 (m, 4H, carbonyl α-CH$_2$), 2.74-2.79 (m, 2H, diallylic CH$_2$), 3.364 (distorted t, J=9.7 and 10.1 Hz, 1H), 3.698 (t, J=9.357 Hz, 1H), 3.85-3.94 (m, 1H), 3.99-4.12 (m, 2H), 4.13-4.21 (dd, J=7.018 and 12.086 Hz, 1H), 4.22-4.28 (dd, J=5.068 and 8.577 Hz, 1H), 4.28-4.35 (m, 1H), 4.37-4.45 (dd, J=2.1 and 11.5 Hz, 1H), 4.501 (t, J=4.679, 1H), 5.19-5.27 (m, 1H, glyceryl methine), 5.27-5.43 (m, 4H, olefinic H). $^{31}$P NMR (162 MHz, CDCl$_3$) δ −0.543. $[\alpha]_D$=+15.4 (c 1.33, CHCl$_3$).

In cognate experiments, chromatographically purified soy phosphatidyl-myo-inositol (1) was used as the starting material, and the 2,3-mono-O-cyclohexylidene and two isomeric di-O-cyclohexylidene derivatives of soy phosphatidyl-myo-inositol were characterized fully. The compound with structure 1-phosphatidyl-2,3:4,5-di-O-cyclohexylidene-myo-inositol (2) (TLC R$_f$ 0.28) was distinguished from the 1-phosphatidyl-2,3:5,6-di-O-cyclohexylidene-myo-inositol isomer by direct comparison of the latter (TLC R$_f$ 0.27) with authentic synthetic 1D-1-(1,2-di-O-oleoyl-sn-glycero-3-phospho)-2,3:5,6-di-O-cyclohexylidene-myo-inositol (prepared by phosphatidylation of 2,3:5,6-di-O-cyclohexylidene-myo-inositol).

The reaction of (2) with succinic anhydride and 4,4,-dimethylaminopyridine (DMAP), and complete deprotection of the 2,3:4,5-di-O-cyclohexylidene groups gave the 6-)-Succinoyl Soy 1-Posphatidyl-*myo*-inositol structure:

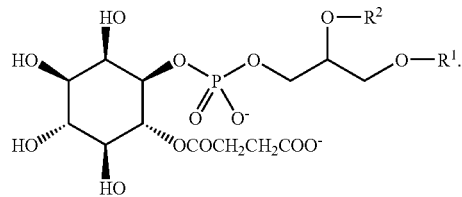

Soy 1-Phosphatidyl-2,3:4,5-di-O-cyclohexylidene-6-O-methoxymethyl-myo-inositol (3). To a solution of (2) (4.1 g, 4.2 mmol) in dry CH$_2$Cl$_2$ (40 ml) and diisopropyethylamine (~26 ml) under N$_2$ atmosphere at 0° C. was added chloromethyl methyl ether (MOMCl) (2.9 g, 36 mmol). After overnight reaction at room temperature (~22° C.) the reaction solution was diluted with CHCl$_3$ (100 ml) and then washed with 1N HCl (50 ml), H$_2$O (2×50 ml) and aq sat NaHCO$_3$ (50 ml) where all solvents used were cold and deoxygenated. The organic extract was dried over Na$_2$SO$_4$, evaporated at 18° C. under reduced pressure then further dried overnight under high vacuum. The material was then purified by chromatography (silica gel, CHCl$_3$/MeOH/NH$_4$OH, 90:10:1, v/v/v) to obtain 3 (1.5 g, 35%; TLC R$_f$=0.30, (CHCl$_3$/MeOH/NH$_4$OH, 90:10:1, v/v/v). MS m/z, 1038.0. $^1$H NMR (400 MHz, ~2:1 CDCl$_3$/CD$_3$OD) δ 0.85-1.0 (m, 6H, CH$_3$), 1.2-1.8 (m, 62H, cyclohexyl and fatty acyl CH$_2$), 2.0-2.1 (m, 4H, allylic CH$_2$), 2.3-2.4 (m, 4H, carbonyl α-CH$_2$), 2.7-2.8 (m, 2H, diallylic CH$_2$), 3.447 (s, 3H, methoxy CH$_3$), 3.47 (m, 1H, overlaps with latter peak), 3.98-4.14 (m, 3H), 4.16-4.25 (m, 2H), 4.3-4.45 (4H, solvent OH overlaps this area), 4.47-4.5 (m, 1H), 4.8-4.8 (m, 2H, MOM H), 5.2-5.3 (m, 1H, glyceryl methine), 5.3-5.4 (m, 4H, olefinic H). $^{31}$P NMR (162 MHz, ~2:1 CDCl$_3$/CD$_3$OD) δ −1.403. $[\alpha]_D$ data not obtained.

The fattyacyls in (3) are retailored by an alkali or lipase enzyme catalyzed hydrolysis and reesterification of the resulting free glyceryl hydroxyls with any desired fattyacyls. Re-esterification with isostearic acid, a fully saturated fatty acid which is unlike stearic acid and is liquid at sub-zero temperatures, gives the 1,2-di-O-isostearoyl analogue (3A) of (3), which gives the series of products (4A)-(7A) analogous with compounds (4)-(7).

Soy 1-Phosphatidyl-2,3-O-cyclohexylidene-6-methoxymethyl-myo-inositol (4). To a stirred solution of 3 (1.5149 g, 1.4575 mmol) in $CHCl_3$ (11.5 ml) under $N_2$ atmosphere was added a solution of p-toluenesulfonic acid (443 mg, 2.33 mmol) in methanol (11.5 ml). After 33 min, when TLC showed complete disappearance of starting material. The reaction solution was cooled in an ice/water bath, quenched with triethylamine (477 mg), and then aq $NaHCO_3$ (400 mg in 5 ml). The latter mixture was partitioned in a $CHCl_3$ (100 ml), MeOH (100 ml), and aq $NaHCO_3$ (1.3 g in 90 ml) mixture, the organic layer concentrated and purified by chromatography (silica gel, $CHCl_3$/MeOH/$NH_4OH$ mixtures to obtain 4 (665 mg, 47.6, TLC $R_f$=0.34, $CHCl_3$/MeOH/$NH_4OH$, 75:25:2, v/v/v.) $^1H$ NMR (400 MHz, $CDCl_3$) δ 0.85-1.0 (m, 6H, $CH_3$), 1.2-1.8 (m, 52H, cyclohexyl and fatty acyl $CH_2$), 1.97-2.10 (m, 4H, allylic $CH_2$), 2.25-2.36 (m, 4H, carbonyl α-$CH_2$), 2.70-2.84 (m, 2H, diallylic $CH_2$), 3.36-3.48 (m, 1H, overlaps with the methoxylmethyl), 3.432 (s, 3H, methoxy $CH_3$), 3.90-4.10 (m, 4H), 4.11-4.23 (m, 2H), 4.25-4.32 (m, 1H), 4.32-4.43 (m, 2H), 4.68-4.78 (d, 1H, J=6.7 Hz, MOM H), 4.79-4.88 (d, 1H, J=6.7 Hz, MOM H), 5.18-5.27 (m, 1H, glyceryl methine), 5.27-5.43 (m, 4H, olefinic H). $^{31}P$ NMR (162 MHz, $CDCl_3$) δ −2.168.

Soy 1-phosphatidyl-2,3-O-cyclohexylidene-myo-inositol and soy 1-phosphatidyl-6-O-methoxymethyl-myo-inositol were obtained from other later fractions of the above chromatographic purification, and were characterized as novel compounds.

Methoxymethylation of (4) with diisopropyethylamine and MOMCl gave a mixture from which the 4-O-MOM and the 5-O-MOM, and the 4,5-di-O-MOM derivatives of (4) were isolated, and respectively used for synthesis of Soy 1-phosphatidyl-myo-inositol-5-phosphate, Soy 1-phosphatidyl-myo-inositol-4-phosphate, and Soy 1-phosphatidyl-myo-inositol-3-phosphate.

Reaction of (4), its 4-O-MOM or 5-O-MOM derivatives with diazomethane gives the corresponding phosphatidyl-OMe esters, and these phosphotriester intermediates are O-phosphorylated and O-deprotected at the myo-inositol-hydroxyls as described below for the phosphodiester compounds (4) and (5); the phosphatidyl-OMe protection is lost and the phosphotriester reverts to phosphodiester on treatment with triethylamine.

Soy 1-Phosphatidyl-2,3-O-cyclohexylidene-6-O-methoxymethyl-myo-inositol-4,5-bis(9-fluorenylmethylphosphate) (5). To a mixture of 4 (256.1 mg, 0.2670 mmol) and 1H-tetrazole (527.5 mg, 7.529 mmol) was added a solution of di-9-fluorenyl N,N-diisopropyl-phosphoramidite (1.95 g, 3.74 mmol) in dry $CH_2Cl_2$ (8.8 ml). The later mixture was left stirring and was judged complete by TLC after 2 h. To the reaction solution at −20° is added a cold −20° solution of tetrabutylammonium periodate (1.50 g, 3.47 mmol) in $CH_2Cl_2$ (3 ml). After 30 min the solution was warmed to and held at room temperature for 15 min, ethylene glycol (excess) was added, the mixture vortex mixed. The solution was partitioned in $CHCl_3$, MeOH, and 5% aq NaCl and the layers separated. The organic layer was evaporated at 0-5° C. and dried under vacuum and over $P_2O_5$. This dried material was dissolved in dry $CH_2Cl_2$ (18 ml) and cooled to ca 0° C. before triethylamine (3.6 ml) was added and then warmed to rt (23° C.). After ca 1.2 h at rt the reaction was judged complete by TLC, and was purified by column chromatography twice (silica gel, $CHCl_3$/MeOH/$NH_4OH$), and repartitioned in $CHCl_3$, MeOH, and 1% aq NaCl, and the organic layer evaporated to yield 5 (87 mg, 27%; TLC $R_f$=0.14, $CHCl_3$/MeOH/$NH_4OH$, 65:35:5 v/v/v). $^1H$ NMR (400 MHz, 3:2 $CDCl_3$/$CD_3OD$) δ 0.86-1.0 (m, 6H, $CH_3$), 1.047 (t, CH3 of n-butylammonium ion), 1.2-1.8 (m, 52H, cyclohexyl and fatty acyl $CH_2$ which overlap with some n-butylammonium ion protons), 1.98-2.11 (m, 4H, allylic $CH_2$), 2.2-2.3 (m, 4H, carbonyl α-$CH_2$), 2.7-2.8 (m, 2H, diallylic $CH_2$), 3.15-3.23 (m, n-butylammonium $N^+CH_2$), 3.323 (s, 3H, methoxy $CH_3$), 3.95-4.8 (complex groups of m, 18H which overlap with solvent OH), 5.20-5.28 (m, 1H, glyceryl methine), 5.28-5.43 (m, 4H, olefinic H), 7.22-7.30 (m, 4H, aromatic H), 7.31-7.39 (m, 4H, aromatic H), 7.67-7.78 (m, 8H, aromatic H). $^{31}P$ NMR (162 MHz, 3:2 $CDCl_3$/$CD_3OD$) δ −0.396 (1P), 0.047 (2P).

Soy 1-Phosphatidyl-2,3-O-cyclohexylidene-6-O-methoxymethyl-myo-inositol-4,5-bisphosphate (6). To a solution of soy 1-phosphatidyl-2,3-O-cyclohexylidene-6-O-methoxymethyl-myo-inositol-4,5-bis(9-fluorenylmethylphosphate) (5) (75.5 mg, 0.0512 mmole) in dry $CH_2Cl_2$ (1 ml) was mixed triethylamine in an equal volume (1 ml) at rt (22° C.). After 5 days at room temperature almost all starting material was converted to 6 as judged by TLC. The reaction solution was purified by chromatography (silicic acid, 200-325 mesh, acid washed-controlled particle size, 20:25:5:5 $CHCl_3$/MeOH/$NH_4OH$/$H_2O$ (v/v)) to obtain 6 (37.3 mg, 65.1%). TLC $R_f$=0.47, silica H treated with 1% potassium oxalate, $CHCl_3$/MeOH/$NH_4OH$+$CO_2$/$H_2O$, 20:25:5:5, v/v/v/v. $[α]_D$=+6.06 (c1.09, 1:1:0.3 $CHCl_3$/$CH_3OH$/$H_2O$). $^1H$ NMR (400 MHz, 1:1:0.3 $CDCl_3$/$CD_3OD$/$D_2O$) δ 0.84-1.02 (m, 6H, $CH_3$), 1.2-1.84 (m, 52H, cyclohexyl and fatty acyl $CH_2$), 1.99-2.14 (m, 4H, allylic $CH_2$), 2.26-2.39 (m, 4H, carbonyl α-$CH_2$), 2.74-2.86 (m, 2H, diallylic $CH_2$), 3.459 (s, 3H, methoxy $CH_3$), 4.0-4.12 (m, 2H), 4.14-4.26 (m, 3H), 4.28-4.35 (m, 1H), 4.16-4.64 (m, 1H, overlapping with solvent OH), ca 4.5 (m, 3H, obscured by solvent OH), 4.755 (br d, J=6.722 Hz, 1H, MOM group $CH_2$), 4.945 (d, J=6.741 Hz, 1H, MOM group $CH_2$), 5.24-5.44 (m, 5H, glyceryl methine and olefinic H), $^{31}P$ NMR (162 MHz, 1:1:0.3 $CDCl_3$/$CD_3OD$/$D_2O$) δ −1.267 (1P), −0.747 (1P), −1.244 (1P).

Soy 1-Phosphatidyl-myo-inositol-4,5-bisphosphate (7). A solution of soy 1-phosphatidyl-2,3-O-cyclohexylidene-6-O-methoxymethyl-myo-inositol-4,5-bisphosphate (6) (33.6 mg) in 1:1:0.3 $CHCl_3$/$CH_3OH$/HCl—$H_2O$ (4 ml of deoxygenated solvent) was converted into the free acid form in $CHCl_3$, and evaporated and dried under vacuum over $P_2O_5$. Ethanethiol (0.5 ml) was added to the dried material (26.7 mg) under $N_2$ blanket at rt (21.6° C.). After 2.6 h the thiol was evaporated and methanol (2×0.5 ml) was added and evaporated under $N_2$ gas stream two times. After the residue was dried under vacuum and purified by chromatography on silicic acid, 200-325 mesh and partitioned in a Folch-type $CHCl_3$, MeOH, 1% aq NaCl mixture. The organic extract was evaporated under $N_2$ gas stream and dried under vacuum overnight to give 7 (13.3 mg, 44.5%). TLC $R_f$=0.32 (silica H treated with 1% potassium oxalate, $CHCl_3$/MeOH/$NH_4OH$+$CO_2$/$H_2O$, 20:25:5:5 v/v/v/v). MS (m/z, negative mode) 496.2 ((M−2)/2), 510.2 ((M+14−2)/2). $^1H$ NMR (400 MHz, 1:1:0.3 $CDCl_3$/$CD_3OD$/$D_2O$) δ 0.8-1.05 (m, 6H, $CH_3$), 1.2-1.4 (m, 38H, fatty acyl $CH_2$), 1.54-1.7 (m, 4H, carbonyl β-$CH_2$), 2.0-2.15 (m, 4H, allylic $CH_2$), 2.25-2.4 (m, 4H, carbonyl α-$CH_2$), 2.75-2.85 (m, 2H not 2H, diallylic $CH_2$), 3.64-3.7 (distorted dd, avg. J=2.77 & 9.76 Hz, 1H, inositol 3-H), 3.9-3.97 (m, 1H), 3.98-4.11 (m, 4H), 4.17-4.24 (m, 2H), 4.27-4.36 (q, 1H, inositol 4-H), 4.4-4.47 (distorted dd, avg. J=2.597 & 12.16 Hz, 1H, glycerol 1'-H, overlaps with solvent OH), 5.2-5.45 (m, 5H, glyceryl methine & olefinic H). $^{31}$P NMR (162 MHz, 1:1:0.3 CDCl$_3$/CD$_3$OD/D$_2$O) δ 0.060 (1P), 1.622 (1P), 2.331 (1P).

The 1,2-di-O-isostearoyl analogue (7A) of (7), is prepared by synthesis from (3A) via (4A)-(6A) as described for synthesis of (7) from 3 via (4) to (6).

Both (7) and (7A) are designed and disclosed now as prototypical phosphatidyl-myo-inositol-phosphates (PIP$_n$s) displaying lyotropic thermotropic mesomorphic transitions, at full hydration, matching those of PIP$_2$ from bovine brain; the latter which is the bench mark assay substrate for PI 3-kinase signaling enzyme family, is based on polyunsaturated fattyacyls and is damaged quickly by non-specific aerial oxidation. The design of (7A) uses isostearic acid, a commercial mixture of branched saturated 18-carbon fatty acids which remains liquid at sub-zero temperatures, and melts slowly (DTA/DSC) between −65 to −30.6° C. (cf. Arachidonic acid m.p. −49.5° C.). Longer and shorter chain analogs of isostearic acid are obtained by standard chemistries. The broad group comprises diisostearoyl-PIP$_n$s and PIP$_n$s wherein at least one of Alk$^1$CO and Alk$^2$CO is isostearoyl and the other is the isostearic acid or a different saturated fattyacyl, or functionalized fattyacyl, e.g., an ω-aminoalkanoyl, or N-substituted derivative thereof.

The group of PIP$_n$ reagents disclosed herein, particularly diisostearoyl-PIP$_2$ (7A) are designed specifically for matrix or surface-spread micro- and nano-array kit-type applications as reagents for in vitro research studies, enzyme assays, and HTS systems based on phosphatidylinositol-phosphates as biological signaling messengers and transducers.

All of the compositions and methods disclosed and claimed herein, can be made and executed by those of ordinary skill in the art without undue experimentation in light of the present disclosure. While the compositions and methods of this invention have been described in terms of preferred embodiments, it will be apparent to those of skill in the art that variations may be applied to the compositions, methods and in the steps or in the sequence of steps of the methods described herein without departing from the concept, spirit and scope of the claimed invention. More specifically, it will be apparent to those of ordinary skill in the art that certain agents that are related chemically, structurally, functionally and/or physiologically, may be substituted for the particular agents described herein in order to yield the same, similar or otherwise beneficial results in accordance with the invention. All such similar substitutes and modifications apparent to those skilled in the art are to be included within the spirit, scope and concept of the invention as defined herein and by the appended claims.

REFERENCES

The following references, to the extent that they provide exemplary procedural or other details supplementary to those set forth herein, are specifically incorporated herein by reference.

Aneja R., Chadha J. S., and Knaggs J. A. 1969, *Biochim. Biophys. Res. Commun*, 36, 401-406.

Aneja R., Chadha J. S., and Davies A. P. 1970, *Biochim. Biophys. Acta*, 218, 102-111.

Aneja R., Chadha J. S., and Yoell R. W. 1971, *Fette Seifen Anstrichmittel*, 73, 643.

Aneja R. 1972, U.S. Pat. No. 3,704,254 (Lever Brothers Company, NY).

Aneja R. 1974, *Biochem. Soc. Trans.*, 2, 38.

Aneja R. and Chadha J. S. 1976, U.S. Pat. No. 28,903 (Lever Brothers Company, NY).

Aneja R. and Aneja S. G. 1999 In *Advances in Phosphoinositides*. Ed. K. S. Bruzik, ACS Symposium Series 718 Washington D.C. 222-231.

Aneja R. and Aneja S. G. 2000, *Tetrahedron Lett.* 41, 847-850.

Aneja R., Cheng J-S, Stoelting D. T. and Zhu W. ACS National Meeting, Boston, Abstract No. 395, Aug. 18-22, 2002.

Aneja R. 2004, U.S. Pat. No. 6,737,536 (Nutrimed Biotech, NY).

Bell R. M., Exton J. H., and Prescott S. M. (Eds.) *Lipid Second Messengers—Handbook of Lipid Research*; Plenum Press: New York, N.Y. 1996, Vol 8.

Berridge M. J. 1984, *Biochem. J*, 220, 345.

Berridge M. J. 1987, *Annu. Rev. Biochem.*, 56, 59.

Berridge M. J. 1993, *Nature*, 361, 315.

Burgess J. W., Neville T. A-M., Rouillard P., Harder Z., Beanlands D. S., and Sparks D. L. 2005, *J. Lipid Res.*, 46: 350-355.

Carter H. E., Johnson P., and Weber E. J. 1965, *Annu. Rev. Biochem.*, 34, 109.

Carter H. E., Strobach R. and Hawthorne J. N. 1969, *Biochemistry*, 8: 383-388.

Carter H. E. and Kisic A. 1969, *J. Lipid Res.*, 10, 356-362.

Clarke N. G., Irvine R. F. and Dawson R. M. 1981, *Biochem. J*, 195: 521-523.

Colacicco G. and Rapport M. M. 1967, *J. Lipid Res.*, 8, 513-515.

Duckworth B. C. and Cantley L. C. *Lipid Second Messengers—Handbook of Lipid Research*; Plenum Press: New York, N.Y. 1996, Vol. 8, 125-175.

Englund P. T. 1993, *Anna. Rev. Biochem.*, 62, 121.

Ferguson M. A. J. and Williams A. F. 1988, *Anna. Rev. Biochem.*, 57, 285.

Ferrari E., Pagella P. G., Maiorana S., and Brufani M. 1993, U.S. Pat. No. 5,214,180 (Mediolanum Farmaceutici, Milan IT).

Gilmanov M. K., Dilbarkanova R., and Sultanbaev B. E. 1990, U.S. Pat. No. 4,977,091.

Hokin L. E. 1985, *Ann. Rev. Biochem.*, 54, 204.

Jett M., Chudzik J., Irving C. R., and Stanacev N. Z. 1985, *Cancer Res.*, 45, 4810.

Jett-Tilton M. 1991, U.S. Pat. No. 4,997,761 (Houston Biotechnology, Inc.).

Jones M., Rana K. K., and Ward J. G. 1989, *Tetrahedron Lett.*, 30, 5353.

Kozikowski A. P., Faug A. H., and Powis G. 1993, U.S. Pat. No. 5,227,508. (Mayo Foundation, Rochester, Minn.).

Lapetina E. G., Billah M. M., and Cuatrecasas P. 1981, *Nature*, 292, 367.

Lee K. D, Hong K., and Papahadjopoulos, D. 1992, *Biochim. Biophys. Acta*, 1103, 185.

Leung L. W., Lin W. Y., Richard C., Bittman R., and Arthur G. 1998a, *J. Liposome Res.*, 8, 213.

Mandala S. M., Thornton R. A., Milligan J., Rosenbach M., Garciacalvo M., Bull H. G., Harries G., Abruzzo G. K., Flattery A. M., Gill C. J., Bartizal K., Dreikorn S., and Kurtz M. B. 1998, *J. Biol. Chem.*, 273, 14942.

Nishizuka Y. 1986, *Science*, 233, 305.

Noda N. and Keenan R. W. 1990, *Chem. Phys. Lipids*, 53, 53-63.

Rhee S. G., Suh P. G., Ryu S. H., and Lee S. Y. 1989, *Science*, 244, 546.

Sachs B. A., Danielson E. and Leiter L. 1960, *J. Appl. Phys.*, 15: 983-986.

Saltiel A. R., Fox J. A., Sherline P., and Cuatrecasas P. 1986, *Science*, 233, 967.

Shimizu S., Yamane T., Li D., and Juneja L. R., 1992 U.S. Pat. No. 5,100,787 (The Nisshin Oil Mills, Ltd. Tokyo, JP).

Small D. M. *The Physical Chemistry of Lipids—Handbook of Lipid Research*; Plenum Press: New York, N.Y. 1986, Vol 4, 475.

Sparks D. L. 2004, U.S. Pat. No. 6,828,306 (Ottawa Heart Institute Research Corporation, Ottawa, Calif.).

Toker A., Meyer M., Reddy K., Falck J. R., Aneja R., Aneja S., Parra A., Burns D. J., and Cantley L. M. 1994, *J. Biol. Chem.*, 269, 32358.

Whitman M., Downes C. P., Keeler M., Keller T., and Cantley L. 1988, *Nature*, 332, 644.

Woolley D. W. 1943, *J. Biol. Chem.*, 147, 581-591.

Yang S. S., Beattie T. R., Durette P. L., Gallagher T. F., and Shen T. Y. 1985, U.S. Pat. No. 4,515,722 (Merck & Co. Inc.).

I claim:

1. A method of isolating and purifying inositolphospholipids (IPL) comprising phosphatidylinositol (PI) from starting materials comprising natural plant source lipids or fractions thereof, wherein said natural plant source lipids or fractions contain IPL, comprising the steps of:
   a. treating said starting materials with an anhydride and separating an alcohol-insoluble precipitate material from an alcohol-soluble extract solution;
   b. repeating said extraction and separation step (a) until said precipitate is substantially free of components that are less polar than PI, wherein said precipitate is a Total-IPL product;
   c. dissolving said Total-IPL product in a two liquid phase aqueous wash, wherein said liquid phases are separated by a solvent partition, wherein one of said liquid phase comprises glycophytosphingolipids (GSL) and the other said liquid phase is substantially free of GSL;
   d. filtering and evaporating part of said liquid phase that is substantially free of GSL to obtain a substantially GSL-free IPL product;
   e. precipitating another part of said liquid phase that is substantially free of GSL, wherein a precipitate is formed comprising phytoglycolipids (PGL) and a supernatant is formed comprising a substantially PGL-free IPL product;
   f. recovering PGL-free IPL filtrate by filtration or PGL-free IPL supernatant by centrifugation and evaporating said filtrate or supernatant to obtain a substantially PGL-free IPL product;
   g. adsorbing on silica remaining PGL and GSL from said substantially PGL-free IPL product to obtain a substantially pure PI product;
   h. eluting said substantially pure PI product with a solvent;
   i. purifying said substantially PGL-free product by isolating in sodium salt form and subjecting said sodium form product to crystallization;
   j. Optionally, step (c) by dissolving Total-IPL in $CHCl_3$, $CH_3OH$, and $H_2O$ to form said two liquid phase aqueous wash, wherein a $CHCl_3$-rich phase is separated and washed with a fresh $CH_3OH$-water phase, and wherein said $CHCl_3$-rich phase is substantially free of GSL; and wherein said substantially PGL-free and substantially GSL-free products comprise from about 1% w/w to about 5% w/w of the said PGL or GSL, respectively.

2. The method of claim 1, wherein said natural source lipids are soybean lecithins.

3. A substantially PGL-free IPL product prepared from soybean lecithins according to claim 2.

4. A method of preparing phosphatidylinositol (PI) products with natural 1D-1(1,2-diacyl-sn-glycero-3-phospho)-myo-inositol stereo-structure from a starting material, wherein said starting material comprises said substantially GSL-free IPL product, substantially PGL-free IPL product, or substantially pure PI product obtained in claim 1, comprising the steps of:
   a. treating said starting material with reagents to affect temporary O-substitution of the inositol hydroxyls of PI with base-stable acid sensitive O-protecting groups to yield an O-protected PI intermediate;
   b. isolating and purifying the said O-protected PI intermediate from the treatment mixture by selective solvent extraction or by passing over/through chromatographic silica;
   c. removing said O-protecting groups from said O-protected PI intermediate by mild acid catalyzed hydrolysis or alcoholysis, and regenerating PI products with natural 1D-1(1,2-diacyl-sn-glycero-3-phospho)-myo-inositol stereo-structure.

5. The method of claim 4 wherein the said base-stable acid-sensitive O-protecting groups are selected from but are not limited to the group comprising tetrahydropyranyl (THP), tetrahydrofuranyl (THF), 4-methoxy-THP, cyclohexylidene, 2-methoxy-cyclohexyl, acetonide, and methoxylmethyl (MOM).

6. An IPL compound, wherein the compound has the absolute stereochemical structure 1D-1-(1,2-di-O-fattyacyl-sn-glycero-3-phospho)-myo-inositol, and wherein one or both hydroxyl groups at myo-inositol positions 4- and 5-carry phosphoric acid residues or salts thereof, and wherein the fatty acid composition and distribution at the sn-glycero-1- and sn-glycero-2-positions are as in Soy phosphatidyl-myo-inositol with the shown 1-O-palmitoyl-2-O-linoleoyl motif as the predominant molecular species:

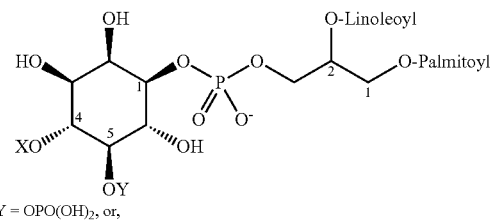

X = Y = OPO(OH)$_2$, or,
X = H, Y = OPO(OH)$_2$, Y = H; or
X = H, Y = OPO(OH)$_2$.

7. An IPL compound comprising the absolute stereochemical structure 1D-1-(1,2-di-O-fattyacyl-sn-glycero-3-phospho)-myo-inositol, wherein one or both hydroxy groups at myo-inositol positions 4- and 5-carry phosphoric acid residues or salts thereof, wherein the group at both the sn-glycero-1- and sn-glycero-2-positions is isostearoyl, and wherein said compound has the structure shown:

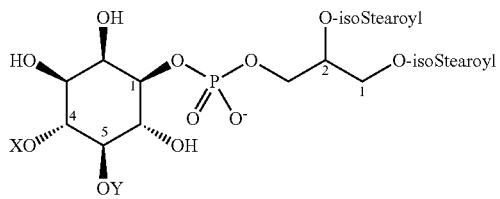

X = Y = OPO(OH)$_2$, or
X = H, Y = OPO(OH)$_2$, Y = H; or
X = H, Y = OPO(OH)$_2$.

8. The IPL compound of claim 7 prepared by mono or bis-phosphorylation of a partially O-protected Soy phosphatidyl-myo-inositol.

9. A partially O-protected Soy phosphatidyl-myo-inositol obtained by selective O-deprotection of O-protected Soy phosphatidyl-myo-inositol wherein the O-protecting groups are selected from orthogonally deprotectable temporary protecting base-stable acid-sensitive groups.

10. An IPL compound, wherein the compound has the absolute stereochemical structure 1D-1-(1,2-di-O-fattyacyl-sn-glycero-3-phospho)-myo-inositol, wherein the 6-hydroxyl group carries at least one functional group or substituent with negative, positive, or neutral net charge selected from the group consisting of phosphate, thiophosphate, sulphate, ω-aminoalkyl and carboxylate, alkyl, and polyethyleneglycol, ω-carboxypropanoyl, (ω-amino-hexylamido)-ω-carboxypropanoyl-, and ω-carboxypropanoyl polyethyleneglycol ester groups, and their respective isoteric molecular and functional group analogues, and wherein said compound is structured to be able to incorporate substituents at the 1,2-O-sn-glycero-positions selected from the group consisting of AlkCO, Alk, and $CH_3O(CH_2)_n$.

11. The IPL compound of claim 10, wherein the said IPL compound carries substituents at either one or both the 2-hydroxyl and the 3-hydroxyl positions, and wherein the said substituents are selected from a group comprising an alkyl or acyl, or replaced by F, Cl, CN, or N-acylamido groups.

12. The IPL compound of claim 10, wherein said respective isoteric molecular and functional group analogues of the phosphate in the phosphatidyl residue comprise C-phosphonate and thiophosphonate residues.

13. The IPL compound of claim 7, wherein at least one of said isostearoyl groups is replaced by a different saturated fattyacyl or a functionalized fattyacyl selected from the group consisting of ω-aminoalkanoyl and N-substituted derivative thereof.

14. A conjugate IPL delivery vehicle, comprising:
a phosphatidylinositol derivative with the following structure:

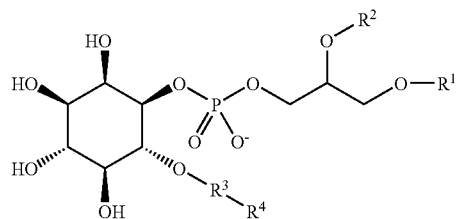

wherein $R^1$=Linoleoyl or isoStearoyl and $R^2$=Palmitoyl or isoStearoyl;
a controlled stability and adjustable chain length linker attached at $R^3$, wherein $R^3$=

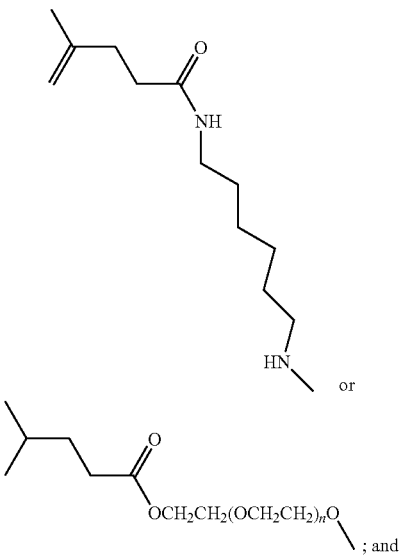

; and a drug that is bioactive towards therapeutic targets in the phosphoinositides cascade or downstream from the phosphoinositide-dependent metabolic and intracellular signaling pathways, and is attached at $R^4$.

15. The conjugate IPL delivery vehicle of claim 14, wherein the therapeutic target comprises protein kinases, phosphatases or allied signaling proteins.

16. The method of claim 1, wherein said natural plant source lipids are seed phosphatides or lecithins, and the said fractions thereof are IPL-enriched.

17. The method of claim 16, wherein said natural plant source lipids are soybean lecithins.

18. The method of claim 16, wherein said fractions thereof are PI-enriched.

19. The conjugate IPL delivery vehicle of claim 14, wherein said phosphatidylinositol derivative comprises a therapeutically active IPL delivery vehicle.

20. The IPL compound of claim 10, wherein said compound is structured to be able to incorporate one or more of the following modifying structural features:
(a) the substituents at the 1,2-O-sn-glycero-positions are selected from AlkCO, Alk, and $CH_3O(CH_2)_n$, or
(b) the substituent at the myo-inositol position 2-, or 3- is selected from the group consisting of Alkyl, Alkoxy, F, Cl, CN, CH2CH2OH, NHOCR.

21. The method of claim 1, wherein said anhydride is selected from the group consisting of acetic, propionic and butyric anhydrides.

* * * * *